US009382580B2

(12) United States Patent
Celedon

(10) Patent No.: US 9,382,580 B2
(45) Date of Patent: Jul. 5, 2016

(54) DETECTION UNITS AND METHODS FOR DETECTING A TARGET ANALYTE

(71) Applicant: Scanogen Inc., Baltimore, MD (US)

(72) Inventor: Alfredo Andres Celedon, Columbia, MD (US)

(73) Assignee: Scanogen Inc., Baltimore, MD (US)

( * ) Notice: Subject to any disclaimer, the term of this patent is extended or adjusted under 35 U.S.C. 154(b) by 96 days.

(21) Appl. No.: 14/352,649

(22) PCT Filed: Oct. 10, 2012

(86) PCT No.: PCT/US2012/059497
§ 371 (c)(1),
(2) Date: Apr. 17, 2014

(87) PCT Pub. No.: WO2013/059044
PCT Pub. Date: Apr. 25, 2013

(65) Prior Publication Data
US 2014/0274795 A1 Sep. 18, 2014

Related U.S. Application Data

(60) Provisional application No. 61/548,488, filed on Oct. 18, 2011.

(51) Int. Cl.
C12Q 1/68 (2006.01)
G01N 33/542 (2006.01)
G01N 33/543 (2006.01)

(52) U.S. Cl.
CPC ............ *C12Q 1/6825* (2013.01); *C12Q 1/6834* (2013.01); *G01N 33/542* (2013.01); *G01N 33/5438* (2013.01); *Y10T 436/143333* (2015.01)

(58) Field of Classification Search
CPC .. C12Q 1/6825; C12Q 1/6834; G01N 33/542; G01N 33/5438; Y10T 436/143333
See application file for complete search history.

(56) References Cited

U.S. PATENT DOCUMENTS

| 7,736,889 B2 | 6/2010 | Rife |
| 2002/0115088 A1 | 8/2002 | Kurn |
| 2003/0207296 A1 | 11/2003 | Park |
| 2004/0234970 A1 | 11/2004 | Yoo |

(Continued)

FOREIGN PATENT DOCUMENTS

| WO | WO 2011045570 A2 | 4/2011 |
| WO | WO 2012071428 A2 | 5/2012 |
| WO | WO 2013059044 A1 | 4/2013 |

OTHER PUBLICATIONS

Lipfert, Jan, Sven Klijnhout, and Nynke H. Dekker. "Torsional sensing of small-molecule binding using magnetic tweezers." Nucleic acids research 38.20 (2010): 7122-7132.*

(Continued)

*Primary Examiner* — Lyle Alexander
*Assistant Examiner* — Robert Eom
(74) *Attorney, Agent, or Firm* — Karta Law Firm, LLC; Glenn E. Karta

(57) ABSTRACT

Detection units and methods for detecting one or more target analytes in a sample are disclosed. The detection unit provides a first and second surface connected by a filament which is capable of binding the target analyte in the sample. The methods provide for the detection of the target analyte through the generation of a detectable signal following the binding of the target analyte to the filament.

5 Claims, 11 Drawing Sheets

(56) References Cited

U.S. PATENT DOCUMENTS

| | | | |
|---|---|---|---|
| 2010/0234234 A1 | 9/2010 | Ferrigno et al. |
| 2010/0253328 A1 | 10/2010 | Celedon et al. |
| 2010/0267169 A1 | 10/2010 | Hajimiri et al. |
| 2011/0015380 A1 | 1/2011 | Vezenov |
| 2012/0115744 A1 | 5/2012 | Raymond |

OTHER PUBLICATIONS

Celedon, Alfredo, et al. "Magnetic tweezers measurement of single molecule torque." Nano letters 9.4 (2009): 1720-1725.*

Celedon, Alfredo et al, Torsional Mechanics of DNA Are Regulated by Small-Molecule Intercalation. J. Phys. Chem., Nov. 24, 2010, vol. 114, No. 50, pp. 16929-16935.

International Search Report and Written Opinion from PCT/US2012/059497 mailed Dec. 26, 2012, 12 pages.

Celedon, Alfredo et al. Torsional Mechanics of DNA Are Regulated by Small-Molecule Intercalation. J. Phys. Chem., Nov. 24, 2010. vol. 114, No, 50, pp. 16929-16935.

International Search Report and Written Opinion from PCT/US2012/059497 mailed Dec. 26, 2012, 11 pages.

Carrasco Pulido, C., et al., "Magnetic Tweezers." In: Encyclopedia of Life Sciences (ELS). John Wiley & Sons, Ltd: Chichester. Apr. 2011.

Lipfert, J, et al., "Quantitative Modeling and Optimization of Magnetic Tweezers." Biophysical Journal, vol. 96, Jun. 2009, 5040-5049.

Han, KC, et al., "Elongated oligonucleotide-linked immunosorbent assay for sensitive detection of a biomarker in a microwell plate-based platform." Dec. 15, 2013, Biosens Bioelectron 50:421-4, Elsevier B.V.

Yang, CJ, et al., "Linear molecular beacons for highly sensitive bioanalysis based on cyclic Exo III enzymatic amplification." Sep. 15, 2011, Biosens Bioelectron 27(1):119-24, Elsevier B.V.

Revyakin, A, et al., "Single-molecule DNA nanomanipulation: Improved resolution through use of shorter DNA fragments." Feb. 2005, Nature Methods, vol. 2 No. 2 pp. 127-138, Cold Spring Harbor Laboratory Press.

Smith, SB, et al., "Direct Mechanical Measurements of the Elasticity of Single DNA Molecules by Using Magnetic Beads." Science, New Series, vol. 258, No. 5085 (Nov. 13, 1992), 1122-1126, American Association for the Advancement of Science.

* cited by examiner

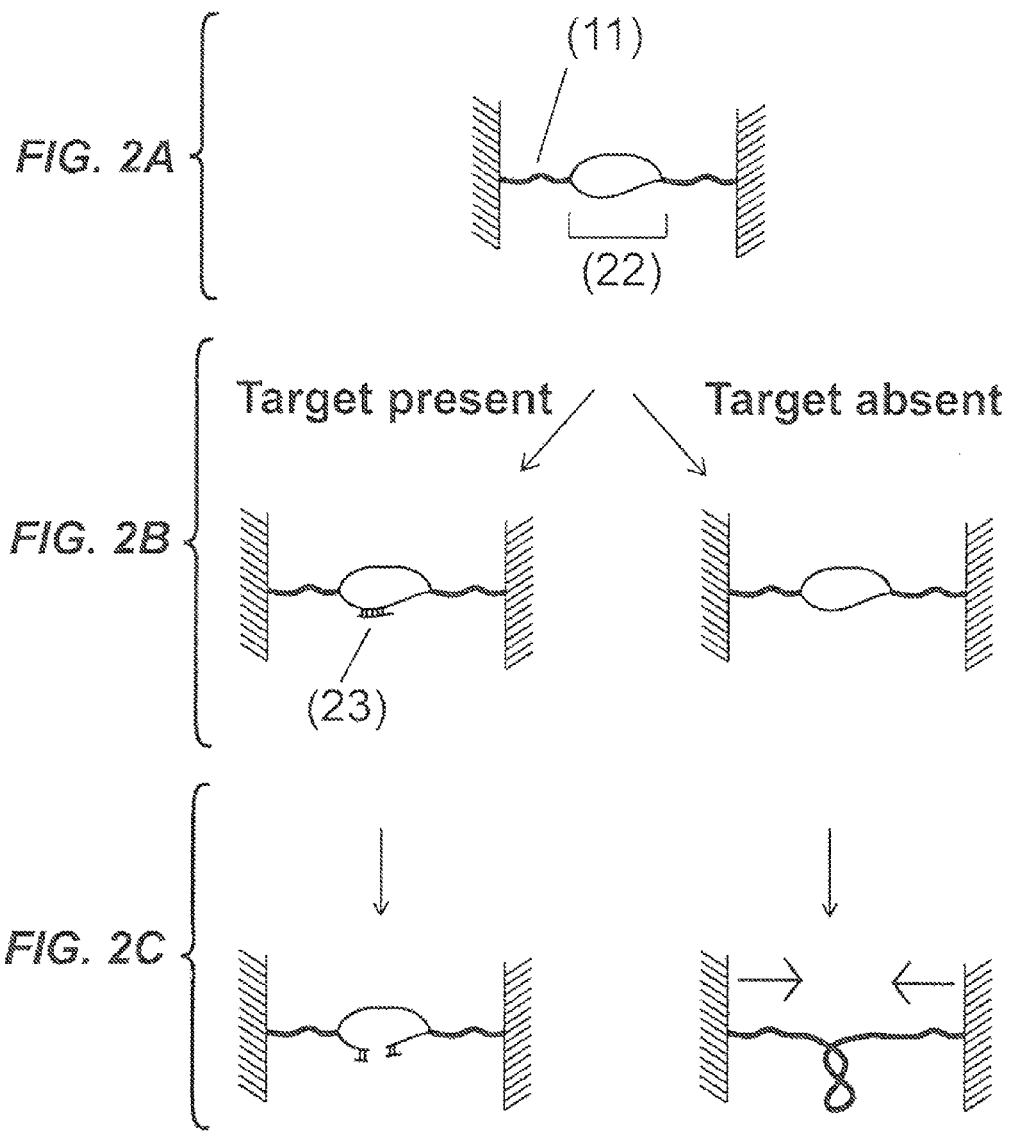

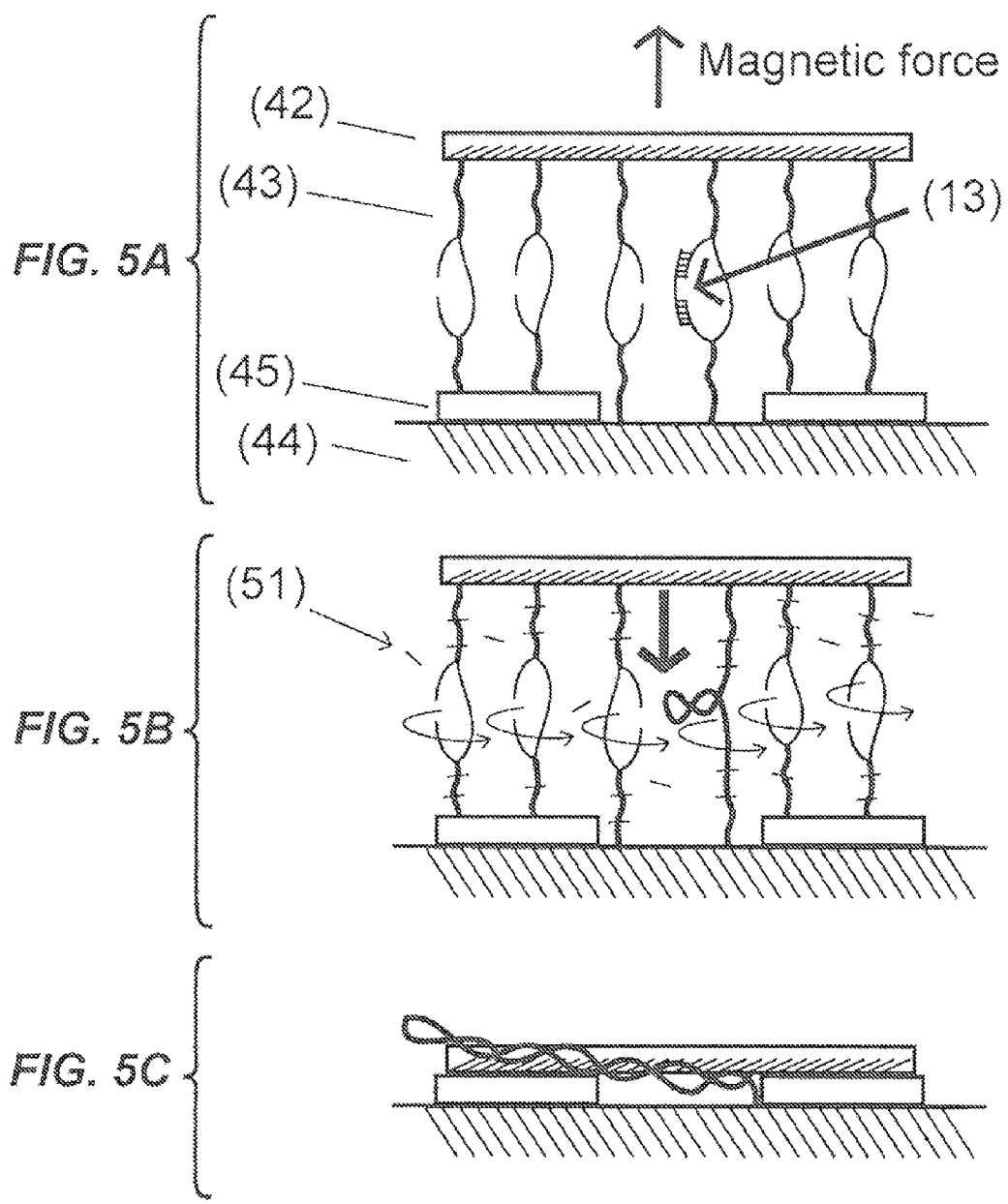

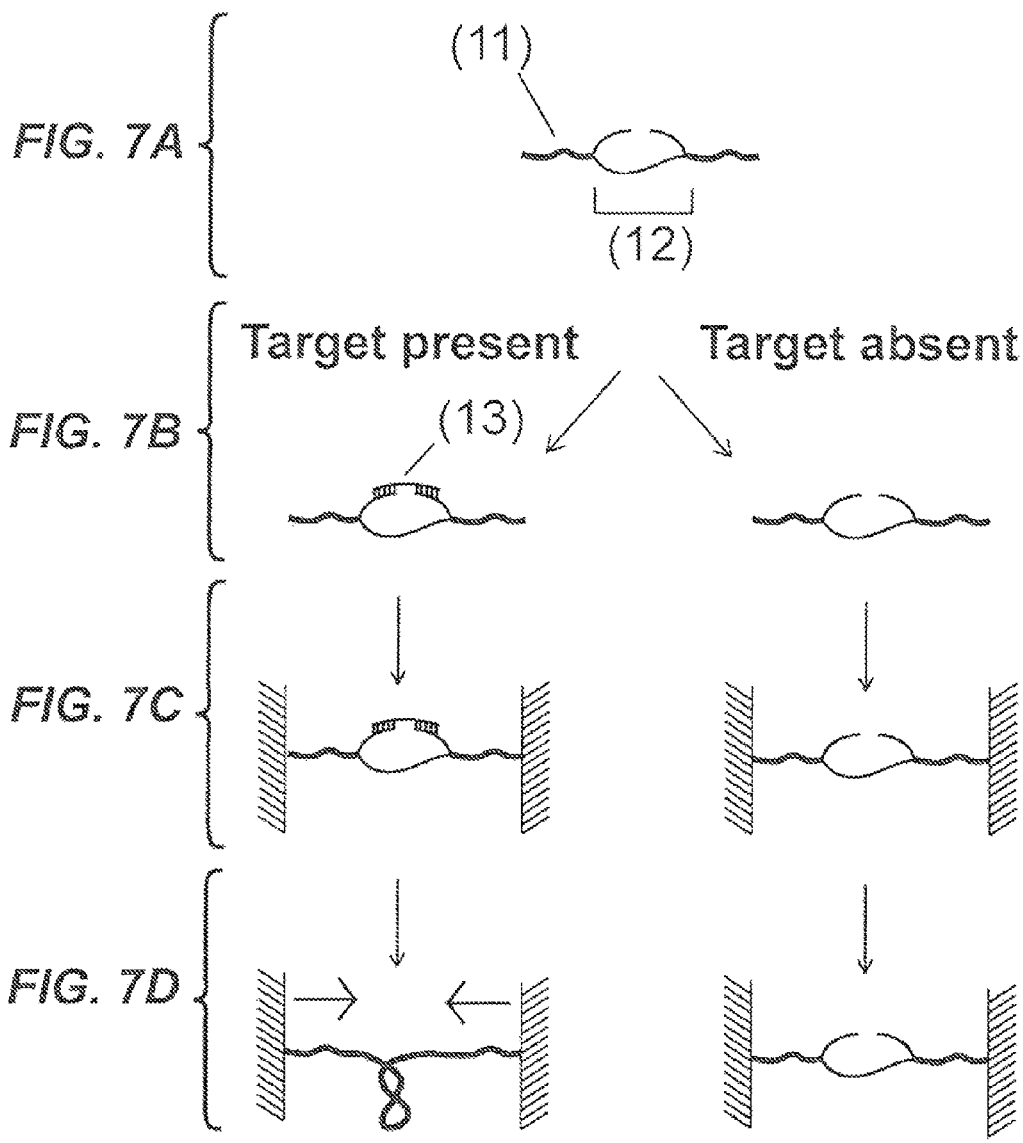

DETECTION UNITS AND METHODS FOR DETECTING A TARGET ANALYTE

CROSS REFERENCE TO RELATED APPLICATIONS

This application is a U.S. National Phase application of PCT/US2012/059497 filed Oct. 10, 2012, which claims the benefit of, and relies on the filing date of, U.S. provisional patent application No.61/548,488, filed Oct. 18, 2011, the entire disclosure of which is incorporated herein by reference.

SEQUENCE LISTING

The instant application contains a Sequence listing, which has been submitted via EFS-Web and is hereby incorporated by reference in its entirety. The ASCII copy of the Sequence Listing, created on 8 Oct. 2012, is named 0169-0001-00304.txt, and is 2 kilobytes in size.

FIELD OF THE INVENTION

The present invention relates generally to detection units and methods for detecting a target analyte such as natural, synthetic, modified or unmodified nucleic acids or proteins in a sample for general diagnostic purposes.

BACKGROUND OF THE INVENTION

Many detection systems for determining the presence or absence of a particular target analyte in a sample are known. Examples of detection systems for detecting analytes include immunoassays, such as an enzyme linked immunosorbent assays (ELISAs), which are used in numerous diagnostic, research and screening applications. Generally, these detection systems detect the target analyte when it hinds to a specific binding agent or probe resulting in a measurable signal.

When using known detection systems, such as immunoassays, the ability to detect a target analyte is often limited by the low concentration of the target analyte in the sample, non-specific binding of the target analyte and background interference generated by other molecules or substances in the sample. The ability to detect a target analyte in a sample taken from biological materials is often limited by most, if not all, of these factors.

Target analytes present in a sample are difficult to detect because the number of potential analytes capable of generating a signal is often limited. A common solution to this problem is to amplify the target analyte using polymerase chain reaction (PCR). However, PCR is only available for nucleic acid analytes and the method takes at least an hour to produce enough of the target analyte to generate a detectable signal in most systems.

The presence of other molecules in the sample can also interfere with the detection of the target analyte by producing background noise. For example, in systems where the detection probe is bound to a surface, a common source of signal interference is the non-specific interaction between molecules in the sample and the surface surrounding the probe.

Purification of a sample is often performed to remove the undesired interfering molecules from the sample in order to better detect the target analyte. However, purification is time consuming, often results in a reduction in the amount of the target analyte in the sample and can alter the concentration of the target analyte in the sample by diluting or concentrating the sample.

Recently, methods and detection systems to selectively detect the presence of a target analyte have been developed, such as those disclosed in U.S. Pub. No. 2009/0011946. In another method, micromechanical devices are used as sensors for detecting physical or chemical changes caused by chemical interactions between natural bio-polymers, which are non-identical binding partners, where one binding partner or probe molecule is placed on a cantilever for possible reaction with a sample analyte molecule. U.S. Pat. No. 6,436,647, "Method for Detecting Chemical Interactions Between Naturally Occurring Biological Analyte Molecules that are Non-Identical Binding Partners." According to this method, a chemical analyte is detected by generating a physical or chemical change, whether through affinity binding, hydrogen bonding, electrostatic attractions, hydrophobic effects, dipole interactions or a heat reaction. The physical or chemical change induces stress on the cantilever which causes the cantilever to move or deflect, which is measured using methods commonly used for detecting cantilever deflection. However, this method requires a relatively high target concentration in the sample since cantilever deflection requires binding of a large number of target molecules. Additionally, the method is prone to non-specific interactions that produce background noise. Since signal generation occurs upon target binding to probes located on a surface, nonspecific binding to the surface can generate signal and background noise.

Accordingly, there is a need for a detection unit and systems of such units as well as methods capable of detecting very low concentrations of target analytes while reducing non-specific binding in the sample.

SUMMARY OF THE INVENTION

In the detection units and methods of this invention, binding of a target analyte to a filament causes a first property change of the filament. Although this property change, in theory, is detectable, it is difficult to detect, due in part to interference from non-specific binding events. Twisting the filament or adding a breaking agent causes a second property change of the filament, such as supercoiling or breaking, which is more easily detected and less likely to be caused by non-specific interactions. Therefore, few target molecules, and in some cases just one target molecule, are enough to produce a detectable signal.

One aspect of the invention relates to a detection unit for identifying a target analyte in a sample. The detection unit comprises a first and second surface connected by at least one filament, wherein the at least one filament comprises at least two strands comprising an active segment, wherein the active segment is capable of binding the target analyte in the sample, wherein the binding of the target analyte in the sample to the active segment causes a first detectable property change of the filament, and wherein the addition of one or more agents or the rotation of the first or second surface causes a second detectable property change of the filament that is transduced to a medium which generates a detectable signal.

In one embodiment of any aspect of the invention, the agent is a twisting agent and/or a breaking agent. According to this embodiment, the twisting agent includes small molecules or an enzyme. According to this embodiment, the breaking agent is a restriction enzyme or restriction endonuclease.

In another embodiment of any aspect of the invention, the physical rotation of the first or second surface where the filament is attached causes the second detectable property change of the filament.

In another embodiment of this aspect of the invention, the detection unit comprises one or more filaments comprising at least one active segment with one or more strands. According to this embodiment, the active segment comprises at least one strand that includes one or more binding sites or optionally includes one or more probes. According to this embodiment, the active segment comprises a continuous single strand and a discontinuous single strand or the active segment comprises two continuous single strands.

In still another embodiment of this aspect, the detection unit contains a filament having an active segment comprising a continuous single strand and a discontinuous single strand. According to this embodiment, the target analyte is capable of binding to the discontinuous single strand and thereby changing the state of the active segment to include two continuous strands. According to this embodiment, after the target analyte is bound to the filament, either a twisting agent is added, which results in an accumulation of torsional stress on the filament, or the physical rotation of the first or second surface where the filament is attached is initiated, which also results in an accumulation of torsional stress on the filament. The accumulation of torsional stress causes the filament to buckle or bend. Once the filament buckles or bends, additional, twisting causes the filament to form supercoils or plectonemes.

According to this embodiment, where the filament of the detection unit is immobilized between the first and second surfaces by attaching the ends of the filament to the two surfaces, then supercoiling causes a detectable change of the force that the filament applies on the surfaces. The supercoiling of the filament, where the distance between the first and second surfaces is not fixed, results in a measurable reduction in the distance between the two surfaces. Alternatively, if the distance is fixed, then a measurable increase in force applied by the filament to the surfaces can be detected.

In still another embodiment of this aspect of the invention, the detection unit comprises a filament having an active segment of two continuous strands. According to this embodiment, binding of the target analyte generates a site recognizable by a breaking agent, for example, a restriction endonuclease, which can cause at least one of the strands to be broken.

In still another embodiment of this aspect of the invention, the detection unit comprises a filament having an active segment comprising only one continuous single strand and a discontinuous single strand. According to this embodiment, binding of the target analyte generates a site recognizable by a breaking agent, for example, a restriction endonuclease, which can break the continuous strand causing a measurable change in the force exerted by the filament.

In one embodiment of any aspects of the invention, target analyte binding occurs prior to attachment of the filament to the detection unit. According to this embodiment, the target analyte is exposed to the filament wherein binding of the analyte to the filament occurs. Following exposure of the target analyte to the filament, the filament is then attached to the detection unit under conditions such that target analyte bound to the filament is not disrupted.

Another aspect of the invention relates to a method for detecting the presence of a target analyte in a sample. According to this aspect of the invention, the method comprises: (a) exposing a sample to at least one detection unit under conditions such that if the target analyte is present in the sample, then it binds to at least one active segment of a filament in a detection unit, wherein binding of the target analyte to the active segment of the filament causes a first detectable change in the property of the filament; (b) exposing the filament to an agent, wherein the exposure of the filament to an agent generates a second detectable change in the property of the filament; (c) transduction of the second detectable change to a medium which generates a detectable signal; and (d) detection of the signal.

Another aspect of the invention relates to a method for identifying or detecting the presence of a target analyte in a sample, the method comprising; (a) providing a filament with an active segment, the filament comprising at least two strands, the active segment having a continuous and discontinuous strand; (b) exposing the filament to the sample under conditions such that if the target analyte is present in the sample, then it either binds to both ends of the discontinuous strand in the active segment or it binds to probes attached at both ends of the discontinuous strand in the active segment; (c) exposing the filament to a twisting agent; and (d) detecting the supercoiling of the filament.

Another aspect of the invention is a method to electrically detect single elongated conductive and semi-conductive nanoparticles. The method consists of providing a substantially flat surface with at least two conductive strips with a non-conductive gap between them. Providing elongated particles with their longest dimension longer than the non-conductive gap, preferably between 100 nm and 10 μm long. One or more particles can get close to the surface when one or more forces act on the particles. Particles on the surface can be detected if they bridge two strips significantly reducing the electrical resistance between them.

BRIEF DESCRIPTION OF THE FIGURES

FIG. 2A depicts a detection unit wherein the filament (11) is attached to two surfaces and includes an active segment (22) with two continuous strands. FIG. 2B depicts exposure of the detection unit to a sample under conditions Such that if the target analyte (23) is present in the sample then it binds to one of the strands in the active segment generating a site that can be recognized by a breaking agent. If the target analyte is not present in the sample, then no change occurs to the active segment. FIG. 2C depicts exposure of the detection unit to a breaking agent and a twisting agent. If the target binds the active segment, then the breaking agent breaks the strand and the active segment comprises a continuous and a discontinuous strands. Therefore, no supercoiling takes place in this case and no significant force is applied on the surfaces. If the active segment still comprises two continuous strands, then supercoiling takes place and a significant force is applied on the surfaces. An active segment having two continuous strands which is converted to one continuous stand and one discontinuous strand due to target binding and exposure to the breaking agent is referred to herein as a "2 to 1 active segment".

FIG. 5A depicts the binding of a target analyte (13) to a discontinuous strand on one of the filaments resulting in two continuous single strands. FIG. 5B intercalating molecules (51) are added which causes the filaments with two continuous single strands to supercoil resulting in a force opposite the magnetic force, which pulls the nanorod closer to the electrodes. FIG. 5C depicts the displacement of the nanorod as a result of filament supercoiling. When the nanorod touches the electrodes, it bridges the two strips which results in a detectable decrease in the electrical resistance between the strips.

FIG. 6B depicts the action of force on one surface (63). Note that this force can be present since the formation of the detection unit or applied at a later step. If the breaking agent breaks the filament then the force is able to move one of the surfaces to which the filament is attached. The change in distance between surfaces can be detected, for example by detecting the presence of the surface that is pulled by the force when it reaches a third surface. If the breaking agent does not break the filament then no significant change in distance between the two surfaces occurs.

FIG. 7A depicts a filament (11) that includes an active segment (12) with a continuous strand and a discontinuous strand. FIG. 7B depicts exposure filament to a sample under conditions such that if the target analyte (13) is present in the sample then it binds to the discontinuous strand in the active segment resulting in two continuous strands. If the target analyte is not present in the sample, then no changes occur to the active segment. FIG. 7C depicts attachment of the filament to a first surface and then to a second surface which produces a detection unit. FIG. 7D depicts exposure of the detection unit to a twisting agent. If the active segment comprises two continuous strands as a result of target binding, then the agent twists the filament which results in supercoiling and a force applied by the filament on the surfaces. If the active segment still comprises a continuous and a discontinuous strand, then no significant force is applied on the surfaces. An active segment having one continuous strand and one discontinuous strand which is converted to two continuous strands due to target binding is referred to herein as a "1 to 2 active segment". Note that for every embodiment of this invention there is an alternative embodiment in which the attachment of the filament to the surfaces occurs after filament exposure to the sample. This is true in particular, for the embodiments depicted in FIGS. 1, 2, 3, 4, 5 and 6.

DETAILED DESCRIPTION OF THE INVENTION

Figure 1A:
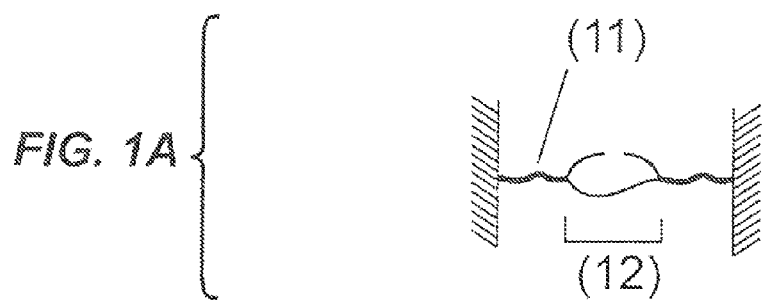
FIG. 1A depicts a detection unit wherein the filament (11) is attached to two surfaces and includes an active segment (12) with a continuous strand and a discontinuous strand.

It should be appreciated that the particular implementations shown and described herein are examples and are not intended to otherwise limit the scope of the application in any way, The published patents, patent applications, websites, company names, and scientific literature referred to herein are hereby incorporated by reference in their entirety to the same extent as if each was specifically and individually indicated to be incorporated by reference. Any conflict between any reference cited herein and the specific teachings of this specification shall be resolved in favor of the latter. Likewise, any conflict between an art-understood definition of a word or phrase and a definition of the word or phrase as specifically taught in this specification shall be resolved in favor of the latter.

As used in this specification, the singular forms "a," "an" and "the" specifically also encompass the plural forms of the terms to which they refer, unless the content clearly dictates otherwise. The terms "about" and "substantially" are used herein to mean approximately, in the region of, roughly, or around. When the terms "about" and "substantially" are used in conjunction with a numerical range, it modifies that range by extending the boundaries above and below the numerical values set forth. In general, the terms "about" and "substantially" are used herein to modify a numerical value above and below the stated value by a variance of less than about 20%.

Technical and scientific terms used herein have the meaning commonly understood by one of skill in the art to which the present application pertains, unless otherwise defined. Reference is made herein to various methodologies and materials known to those of skill in the art. Standard reference works setting forth the general principles of recombinant DNA technology include Sambrook et at, "*Molecular Cloning: A Laboratory Manual*," 2nd Ed., Cold Spring Harbor Laboratory Press, New York (1989); Kaufman et al., Eds., "*Handbook of Molecular and Cellular Methods in Biology in Medicine*," CRC Press, Boca Raton (1995); and McPherson, Ed., "*Directed Mutagenesis: A Practical Approach*," IRL Press, Oxford (1991), the disclosures of each of which are incorporated by reference herein in their entireties.

The invention pertains to a novel detection unit comprising a first and second surface connected by at least one filament. The filament has at least two strands which have at least one active segment. The invention further pertains to methods of identifying a target analyte in a test sample utilizing the detection unit(s) described herein.

Preferably, the detection unit is useful to identify a target analyte in a sample. The detection unit may contain a first and second surface connected by at least one filament, wherein the filament has at least two strands having an active segment, wherein the active segment is capable of binding the target analyte in the sample, and wherein the binding of the target analyte in the sample to the active segment causes a detectable property change of the filament. The filament may be immobilized between the first and second surfaces by attaching the ends of the filament to the two surfaces. Upon binding of the target analyte to one of the filaments, the addition of an agent causes another detectable property change of the filament that generates a detectable signal.

The terms "target analyte" or "analyte," are used herein to denote the molecule or atom to be detected in the test sample. According to the invention, there can be one, two, three, four, five, ten, fifteen, twenty, hundred, thousand or more different target analytes in the test sample. The target analyte can be any molecule or atom for which there exists a naturally or artificially prepared specific binding member. Examples of target analytes include, but are not limited to, a nucleic acid, oligonucleotide, DNA. RNA, protein, peptide, polypeptide, amino acid, antibody, carbohydrate, hormone, steroid, toxin, vitamin, any drug administered for therapeutic and illicit purposes, a bacterium, a virus, cell, as well as any antigenic substances, haptens, antibodies, metabolites, and combinations thereof.

In a preferred embodiment, the target analyte is a nucleic acid. The nucleic acid can be from any source in purified or unpurified form including DNA (dsDNA and ssDNA) and RNA, including tRNA, mRNA, RNA, siRNA, mitochondrial DNA and RNA, chloroplast DNA and RNA DNA-RNA hybrids, or mixtures thereof, genes, chromosomes, plasmids, the genomes of biological materials, including microorganisms such as bacteria, yeast, viruses, viroids, molds, fungi, plants, animals, humans, and fragments thereof. The target analyte can be obtained from various biological materials by procedures well known in the art.

The terms "test sample" or "sample" are used interchangeably herein and include, but are not limited to, biological samples that can be tested by the methods of the present invention described herein and include human and animal body fluids such as whole blood, serum, plasma, cerebrospinal fluid, urine, lymph fluids, and various external secretions of the respiratory, intestinal and genitourinary tracts, tears, saliva, milk, white blood cells, myelomas and the like, biological fluids such as cell culture supernatants, fixed tissue specimens and fixed cell specimens, PCR amplification products or a purified product of one of the above samples. A "sample" may include gaseous mediums, such as ambient air, chemical or industrial intermediates, chemical or industrial products, chemical or industrial byproducts, chemical or industrial waste, exhaled vapor, internal combustion engine exhaust, or headspace vapor such as vapor surrounding foods, beverages, cosmetics, vapor surrounding plant or animal tissue and vapor surrounding a microbial sample. Additional sample mediums include supercritical fluids such as supercritical $CO_2$ extricate. Other exemplary mediums include liquids such as water or aqueous solutions, oil or petroleum products, oil-water emulsions, liquid chemical or industrial intermediates, liquid chemical or industrial products, liquid chemical or industrial byproducts, and liquid chemical or industrial waste. Additional exemplary sample mediums include semisolid mediums such as animal or plant tissues, microbial samples, or samples containing gelatin, agar or polyacrylamide.

The terms "first and second surface," "surface," "first surface" and "second surface" are used herein to denote any material suitable for being connected by at least one filament and which are amenable to at least one detection method disclosed herein. The number of possible suitable materials is large and would be readily known by one of ordinary skill in the art.

In exemplary embodiments, the surface may be composed of modified or functionalized glasses, inorganic glasses, plastics, including acrylics, polystyrene and copolymers of styrene, polypropylene, polyethylene, polybutylene, polyurethanes, Teflon, polysaccharide,s, nylon or nitrocellulose, resins, and other polymers, carbon, metals, ceramics, silica or silica-based materials including silicon and modified silicon and silicon wafers. The surfaces can be functionalized by a monolayer of one or more molecules. Methods of producing self-assembled monolayers are well known in the art. In particular, there are several known methods to assemble monolayers of thiolates on metal surfaces. See e.g., Love, J. C. et al., Chem. Rev., 105, 1103 (2005). The surface can be a composite material. For example, superparamagnetic microscale beads, which are well known in the art, consisting of iron oxide nanoparticles dispersed in a polystyrene matrix.

The surface can be a silicon wafer with an insulating layer, such as an oxide layer, produced on the wafer by a wet thermal environment, although an insulating layer is not necessarily critical to all embodiments of the detection unit. Additional insulating layers include, but are not limited to, silicon nitride and polyamide.

According to another embodiment, the surface may be a nonconductive material with a conductive or semiconductive pattern fabricated using methods well known in the art, such as photolithography. For example, it can be a glass with a conductive pattern of a metal, such as gold, platinum, chromium or copper.

In another exemplary embodiment, the surface is a nanoparticle. As used herein a nanoparticle is a particle with at least one dimension less than 1 µm, such as a nanorod, nanowire, or nanosphere. According to this embodiment, the nanoparticle is made of one or more metals, each part of the particle is of a different metal. The metals can be electrical conductor, such as gold, silver, copper and platinum, semiconductor, for example cadmium selenide (CdSe), cadmium sulfide (CdS) or CdSe or CdS coated materials with zinc sulfide (ZnS). In additional embodiments, the metals can be magnetic, such as iron, iron oxides or nickel. In additional embodiments, the nanoparticle comprises zinc oxide (ZnO), titanium dioxide ($TiO_2$), silicone (Si), indium nitride (InN), silver iodide (AgI), silver bromide (AgBr), mercuric iodide ($HgI_2$), lead sulfide (PbS), lead selenide (PbSe), zinc telluride (ZnTe), cadmium telluride (CdTe), $In_2$, $S_3$, Cadmium phosphide ($Cd_3P_2$), cadmium ($Cd_3$), $As_2$, indium arsenide (InAs), GaAs or gallium nitride (GaN).

In a preferred embodiment the nanoparticle is conductive or semi-conductive and has an elongated shape, such as a nanorod or nanowire. Publication US 2004/0014106 A1 describes a method to electrically detect the presence of nanoparticles when they contact a surface. In this publication, the presence of nanoparticles is detected when they bridge two patterned conductors separated by a non-conductive gap. However, single spherical nanoparticles are not able to bridge non-conductive gaps between patterned conductors and therefore more than one particle are needed and/or one additional Silver enhancement step is needed to electrically connect the two conductors and detect the presence of the particles.

According to this embodiment, a method is provided to electrically detect single elongated conductive and semi-conductive magnetic nanoparticles. The method consists on providing a substantially flat surface with at least two conductive strips with a non-conductive gap between them. Providing elongated particles with their longer dimension longer than the non-conductive gap, preferably between, 100 nm and 10 µm long. One or more particles can get close to the surface when one or more forces act on the particles. Particles on the surface can be detected if they bridge two strips significantly reducing the electrical resistance between them. The longer dimension of the nanoparticles can be chosen considering the width of the conductive strips and non-conductive gaps to ensure that most nanoparticles on the surface bridges at least two strips. The number of nanoparticles bridging two strips can be inferred from the decrease on electrical resistance between the strips. Two electrodes with interdigitated strips instead of a pair of strips can be used to increase the number of non-conductive gaps between, electrodes (FIG. 2b in Publication US 2004/0014106 A1). The particles can have different electrical properties to allow for identification of the specific type of particle that is bridging the electrodes. For example, type 1 particles have an electrical resistance of 1 kΩ while type 2 particle have an electrical resistance of 100 kΩ. The number of type 1 particles and the number of type 2 particles contacting two conductive strips can be estimated from the total electrical resistance between strips.

In an aspect of this detection method, the particles can have at least one segment of a magnetic material which gives the particles a magnetic moment. In this aspect, a magnetic field is provided that orients the magnetic particles substantially perpendicular to the conductive strips and substantially parallel to the surface. If the particles are substantially perpendicular to the strips, it can be ensured that each particle on the surface bridges at least two strips.

Methods of making metal, semiconductor and magnetic nanoparticles are well-known in the art. See, e.g., Schmid, G. (ed.) *Clusters and Colloids* (V C H, Weinheim, 1994); Hayat, M. A. (ed.) *Colloidal Gold: Principles, Methods, and Applications* (Academic Press, San Diego, 1991); Massart, R., *IEEE Taransactions On Magnetics*, 17, 1247 (1981); Abmadi, T. S. et al., Science, 272, 1924 (1996); Henglein, *A. et al., J. Phys. Chem.*, 99, 14129 (1995); Curtis, A. C., et al., Angew. Chem. Int. Ed. Engl., 27, 1530 (1988).

Methods of making ZnS, ZnO, $TiO_2$, AgI, AgBr, $HgI_2$, PbS, PbSe, ZnTe, CdTe, $In_2S_3$, $In_2$, $Se_3$, $Cd_3$, $P_2$, $Cd_3$, $As_2$, InAs, and GaAs nanoparticles are also known in the art. See, e.g., Weller, Angew. Chem. Int. Ed. Engl., 32, 41 (1993); Henglein, Top. Curr. Chem., 143, 113 (1988); Henglein, Chem. Rev., 89, 1861 (1989); Brus, Appl. Phys. A., 53, 465 (1991); Bahncmann, in Photochemical Conversion and Storage of Solar Energy (eds. Pelizetti and Schiavello 1991), page 251; Wang and Herron, J. Phys. Chem., 95, 525 (1991); Olshaysky et al., J. Am. Chem. Soc., 112, 9438 (1990); Ushida et al., J. Phys. Chem., 95. 5382 (1992). Suitable nanoparticles are also commercially available from, e.g., Ted Pella, Inc. (gold), Amersham Corporation (gold) and Nanoprobes, Inc. (gold).

Methods of making nanorods or nanowires are known in the art. See for example, Halm and Mieber, Nano Lett, 4, 51-54 (2004) (silicon nanorods); Li et al., Appl. Phys. Lett. 4, 4014-1016 (2003) (In2O3 nanorods); Liu et al., Phys. Ev. B. 58, 14681-14684 (1998) (Bismuth nanorods); Sun et al., Appl. Phys. Lett. 74, 2803 (1999) (Nickel nanorods); Ji et al., J. Electrochem. Soc. 150, C523-528 (2003) (AuAg multilayers and multisegment nanorods); Celedon et al Nano Lett., 9, 1720-1725 (2009) (PtNi multisegment nanorods); O'Brien et al., Adv. Mater. 18, 2379-2383 (2006) (polymer nanorods); Liu et al. Nanotechnology 20, 415703 (2009) (superparamagnetic and ferromagnetic Ni nanorods).

Methods of making carbon nanotubes and carbon nanotubes composites are known in the art. See for example, Milo et al., Adv. Mater., 11, 937-941 (1999); Stevens Apt. Phys. Lett., 77, 3453-3455 (2000).

The surfaces and/or, the filaments, are functionalized in order to attach the filaments to the surfaces. Such methods are known in the art. For instance, if the filaments are nucleic acids, they can he functionalized with alkanethiols at their 3'-termini or 5'-termini for attachment to gold surfaces. See, for example, Whitesides, Proceedings of the Robert A. Welch Foundation 39th Conference On Chemical Research Nanophase Chemistry, Houston, Tex., pages 109-121 (1995). See also Mucic et al., Chem. Commun. 555-557 (1996) (describes a method of attaching 3' thiol DNA to flat gold surfaces; this method can be used to attach oligonucleotides to nanoparticles). The alkanethiol method can also be used to attach oligonucleotides to other metal, semiconductor and magnetic colloids and to the other nanoparticles listed above. Other functional groups tier attaching oligonucleotides to solid surfaces include phosphorothioate groups (see, e.g., U.S. Pat. No. 5,472,881 for the binding of oligonucleotide-phosphorothioates to gold surfaces), substituted alkylsiloxanes (see, e.g. Burwell, Chemical Technology, 4, 370-377 (1974) and Matteucci and Caruthers, J. Am. Chem. Soc., 103, 3185-3191 (1981) for binding of oligonucleotides to silica and glass surfaces, and Grabar et al., Anal. Chem., 67, 735-743 for binding of aminoalkylsiloxanes and for similar binding of mercaptoaklylsiloxanes)-. Oligonucleotides terminated with a 5' thionucleoside or a 3' thionucleoside may also be used for attaching oligonucleotides to solid surfaces.

Filaments may be attached to surfaces using the biotin-streptavidin interaction. For example, biotin-labeled filaments are put in contact with streptavidin functionalized surfaces; the biotin-streptavidin interaction attaches the filament to the surface. The following reference describes the attachment of biotin labeled oligonucleotides to a streptavidin functionalized surface. Shaiu et al., Nucleic Acids Research, 21, 99 (1993). Digoxigenin and anti-Digoxigenin antibodies can also be used to attach filaments to surfaces.

The following references describe other methods that may be employed to attach oligonucleotides to surfaces and in particular to nanoparticles: Nuzzo et al, J. Am. Chem. Soc., 109. 2358 (1987) (disulfides on gold); Allara and Nuzzo, Langmuir, 1, 45 (1985) (carboxylic acids on aluminum); Allara and Tompkins, J. Colloid Interface Sci., 49, 410-421 (1974) (carboxylic acids on copper); Her, The Chemistry Of Silica, Chapter 6, (Wiley 1979) (carboxylic acids on silica); Timmons and Zisman, J. Phys. Chem., 69, 984-990 (1965) (carboxylic acids on platinum); Soriaga and Hubbard, J. Am. Chem. Soc., 104, 3937 (1982) (aromatic ring compounds on platinum); Hubbard, Ace. Chem. Res., 13, 177 (1980) (sulfolanes, sulfoxides and other functionalized solvents on platinum); Hickman et al., J. Am. Chem. Soc., 111, 7271 (1989) (isonitriles on platinum); Maoz and Sagiv, Langmuir, 3, 1045 (1987) (silanes on silica); Maoz and Sagiv, Langmuir, 3, 104 (1987) (silanes on silica); Wasserman et al., Langmuir, 5, 1074 (1989) (silanes on silica); Eltekova and Eltekov, Langmuir, 3, 951 (1987) (aromatic carboxylic acids, aldehydes, alcohols and methoxy groups on titanium dioxide and silica); Lee et al., J. Phys. Chem., 92, 2597 (1988) (rigid phosphates on metals).

In order to introduce rotations into a linear filament attached at both ends to surfaces, the filament should be attached by at least two connections to each surface. If the filament is attached by a single connection then the single connection may swivel. Multiple connections can be obtained by filaments containing multiple chemical groups able to interact with a surface. For example, multiple biotin labels at one end of the filament and multiple digoxigenin labels at the other end allow attaching an oligonucleotide by multiple connections at surfaces functionalized with streptavidin and antidigoxigenin, respectively. Methods to produce oligonucleotides functionalized in this manner are well known in the art. See for example. Revyakin, et al, Nat. Methods, 2,127-138 (2005) and Celedon et al., Nano Lett., 9,1720-1725 (2009).

Oligonucleotides of defined sequences are used for a variety of purposes in the practice of the invention. Methods of making oligonucleotides of a predetermined sequence are well-known. See, e.g., Sambrook et al., Molecular Cloning: A Laboratory Manual (2nd ed, 1989) and F. Eckstein (ed.) Oligonucleotides and Analogues, 1st Ed. (Oxford University Press, New York, 1991). Solid-phase synthesis methods are preferred for both oligoribonucleotides and oligodeoxyribonucleotides (the well-known methods of synthesizing DNA are also useful for synthesizing RNA). Oligoribonucleotides and oligodeoxyribonucleotides can also be prepared enzymatically.

As used herein, "a detectable signal" which can be generated according to the invention includes, but is not limited to an electrical (e.g., capacitance), mechanical, optical, acoustic or thermal signal. In a preferred embodiment the detectable signal is electrical.

The term "filament" is used herein to denote at least two, three, four, five, six, seven, eight, nine, ten, twenty, thirty or more "strands". The term "strand" is used to denote a molecule substantially similar to a polymer. The term polymer is used herein to denote a molecule formed by covalently linking monomer units of one or more types into chains. Instead, a "strand" as used herein, can incorporate some molecules different to the basic monomers and these different molecules can be non-covalently linked to the rest of the structure. Examples of monomers that can be used to produce "polymers" useful in the invention can be found in U.S. Patent Publication No. U.S. 2009/0011946, which is herein incorporated by reference in its entirety. According to the invention, the detection unit has at least one first and second surface connected by at least two five, ten, fifteen, or twenty, twenty-five, fifty, hundred, thousand or more filaments.

The filament is preferably a length of about 0.1 µm to about 2 cm, about 100 µm to about 1 cm. More preferably, the filament length is about 1 µm to about 3 µm.

Preferably, the strands of the filament are capable of interacting with one another, for example by Watson-Crick base pairing. Interaction between the strands facilitates the formation of plectonemes or supercoiling when the filament is twisted. The filament can be twisted by rotating one of the surfaces to which the filament is attached. Alternatively, the filament can be twisted by small molecules that hind to the filament. For example, double stranded nucleic acids can be twisted by molecules that intercalate between base pairs and unwind the double helix. Alternatively, double stranded nucleic acids can he twisted by topoisomerases enzymes. Generally, the formation of plectonemes or supercoiling results in an increase of tension in the filament which results in a measurable attractive force between the two surfaces.

Preferably, the strands of the filament are substantially linear polymers. A linear polymer is a molecule formed by monomers in which each monomer is covalently linked with two other monomers, with the exception of the first and the last monomers which are linked to just one other monomer.

The term "monomer" is used herein to refer to a single molecule that has the ability to combine with identical or other molecules in a process known as polymerization. The polymerization reaction may be a dehydration or condensation reaction (due to the formation of water ($H_2O$) as one of the products) where a hydrogen atom and a hydroxyl (—OH) group are lost to form $H_2O$ and an oxygen molecule bonds between each monomer unit.

The term "monomer" includes any chemical group that can be assembled into a polymer. A wide variety of monomers may be used for synthesizing a polymer. For example, a polymer of the invention may be composed of monomers that have, for example, affinity property groups, hydrophilic groups, and/or hydrophobic groups pendant from their backbones. Accordingly, a polymer may include side chains "R" pendant from a structurally repetitive backbone. Exemplary backbones with side chains include:

—(CO—N(—R)—CH$_2$)—;

—(O—Si(—CH$_3$)(—R))—;

—(CH$_2$—CH(—R)—CO—NH)—;

—(CH$_2$—CH(—R)-O)—; and

—(CH$_2$—C$_6$H$_4$—CO—N(—R))—.

—(CH$_2$—CHR)—, or —(CH$_2$—CH$_2$—CHR)—;

—(CF$_2$—CFR), or —(CF$_2$—CF$_2$CFR)—; and

—(CH$_2$CH(—CO—NHR))—.

Additional examples of suitable monomers include, but are not limited to, those described in the references cited in this written description and incorporated by reference herein. Nomenclature pertinent to molecular structures, as well as description of monomers and side chain structures useful for the present invention can be found in U.S. Patent Publication No U.S. 2009/0011946, which is hereby incorporated by reference in its entirety.

Methods of assembling sequence specific polymers for use as probes in the present invention are known in the art (see e.g., U.S. Patent Publication No. US 2009/0011946).

Additionally, a variety of techniques known by one of skill in the art can be used to determine the type and property of the polymer useful in the present invention. Techniques such as wide angle X-ray scattering, small angle X-ray scattering, and small angle neutron scattering are used to deter mine the crystalline structure of polymers. Gel permeation chromatography is used to determine the number average molecular weight, weight average molecular weight, and polydispersity. FTIR, Raman and NMR can be used to determine composition.

Examples of polymers useful in the invention are known by one of skill in the art and include, but are not limited to, natural and synthetic materials. In a preferred embodiment, the polymer is a biopolymer. According to this embodiment, the biopolymer is selected from the group comprising polysaccharides, polypeptides, and polynucleotides.

The polymers of the invention can be a combination of polymers in which different types of polymers (polysaccharides, polypeptides, polynucleotides and any types of synthetic polymers) are attached to each other either covalently or non-covalently.

As used herein, the term "polysaccharides" refers to polymeric carbohydrate structures, formed of repeating units (either mono- or di-saccharides) joined together by glycosidic bonds. Polysaccharides of the invention are preferably linear, but may contain various degrees of branching. Additionally, polysaccharides are generally heterogeneous, containing slight modifications of the repeating unit. Examples of polysaccharides suitable for the invention include homopolysaccharides or homoglycans, where all of the monosaccharides in a polysaccharide are the same type, and heteropolysaccharies or heteroglycans, where more than one type of monosaccharide is present. In exemplary embodiments, the polysaccharide is a starch, glycogen, cellulose, or chitin.

Polysaccharides of the invention have the general formula of $C_x(H_2O)_y$ where X is about 100 to about 100,000, about 200 to about 10,000, about 500 to about 5,000, or about 1,000 to about 2,000. in another embodiment, polysaccharides have repeating units in the polymer backbone of about six-carbon monosaccharides and can be represented by the general formula of $(C_6H_{10}O_5)_n$ where n is about 30 to about 100,000, about 200 to about 10,000, about 500 to about 5,000, or about 1,000 to about 2,000.

As used herein, the terms "polynucleotide," "oligonucleotide," "nucleic acid" and "nucleic acid molecule" are used interchangeably herein to refer to a polymeric form of nucleotides of any length, and may comprise ribonucleotides, deoxyribortucleotides, analogs thereof, or mixtures thereof. This term refers only to the primary structure of the molecule. Thus, the term includes triple-, double- and single-stranded deoxyribonucleic acid ("DNA"), as well as triple-, double- and single-stranded ribonucleic acid ("RNA") or RNArDNA hybrids. It also includes modified, for example by alkylation, and/or by capping, and unmodified forms of the polynucleotide. More particularly, the terms "polynucleotide," "oligonucleotide," "nucleic acid" and "nucleic acid molecule" include polydeoxyribonucleotides (containing 2-deoxy-D-ribose), polyribonucleotides (containing D-ribose) including tRNA, rRNA, siRNA, and mRNA, whether spliced or unspliced, any other type of polynucleotide which is an N- or C-glycoside of a purine or pyrimidine base, and other polymers containing nonnucleotidic backbones, for example, polyamide (e.g., peptide nucleic acids (PNAs)) and polyinorpholino (commercially available from the Anti-Virals, Inc., Corvallis, Oreg., as Neugene) polymers, and other synthetic nucleic acid polymers providing that the polymers contain nucleobases in a configuration which allows for base pairing and base stacking, such as is found in DNA and RNA. The term nucleotides include hybrids thereof, for example between PNAs and DNA or RNA, and also include known types of modifications, for example, labels, alkylation, "caps," substitution of one or more of the nucleotides with an analog, internucleotide modifications such as, for example, those with uncharged linkages (e.g., methyl phosphonates, phosphotriesters, phosphoramidates, carbamates, etc.), with negatively charged linkages (e.g., phosphorothloates, phosphorodithioates, etc.), and with positively charged linkages (e.g., aminoalkylphosphoramidates, am inoalkylphosphotriesters), those containing pendant moieties, such as, for example, proteins (including enzymes (e.g. nucleases), toxins, antibodies, signal peptides, poly-L-lysine, etc.), those with intercalators (e.g., acridine and psoralen), those containing chelates (e.g., metals, radioactive metals, boron, oxidative metals, etc.), those containing alkyiators, those with modified linkages (e.g., alpha anomeric nucleic acids, etc.).

As used herein, the term "polypeptides" refers to a polymer formed from the linking, in a defined order, of preferably, α-amino acids, D-, L-amino acids and combinations thereof. The terms "peptides," "oligopeptides," and "proteins" are included within the definition of polypeptide. The term includes polypeptides containing post-translational modifications of the polypeptide, for example, glycosylations, acetylations, phosphorylations, and sulphations. In addition, protein fragments, analogs (including amino acids not encoded by the genetic code, e.g. homocysteine, ornithine, D-amino acids, and creatine), natural or artificial mutants or variants or combinations thereof, fusion proteins, derivatized residues (e.g. alkylation of amine groups, acetylations or esterifications of carboxyl groups) and the like are included within the meaning of polypeptide. The link between one amino acid residue and the next is referred to as an amide bond or a peptide bond. The terms do not refer to a specific length of the polypeptide.

As used herein, the term "active segment" refers to the region of a filament where binding of the target analyte occurs. Preferably, the region of the filament containing the active segment has at least one continuous and at least one discontinuous strand or has at least two continuous strands. As used herein, the term "continuous strand" refers to one strand having one first and one last monomer connected by a continuous chain of molecules linked to one another by covalent or non-covalent bonds. The molecules of the chain are not necessarily all of the same type of the monomers. As used herein, the term "discontinuous strand" refers to a strand having one first and one last monomer for which there is not a continuous chain of molecules linked to one another by covalent or non-covalent bonds, however, adding one covalent or non-covalent bond is enough to make the "discontinuous strand" become "continuous". The term "non-covalent bond" refers here to an intermolecular interaction with free energy of at least 1 kcal/mol.

Only filaments comprising at least two continuous strands are able to accumulate torsional stress and/or supercoil when twisted. Single stranded filaments, for example alkane molecules, peptide chains or single stranded DNA, do not supereoil because the atoms of the single strand form a single bond and therefore are free to rotate around the axis of the bond. Consequently, as twisting is induced, no torsional stress is accumulated in the filament.

Filaments, comprising at least two continuous strands, have a key difference when exposed to a twisting agent or rotated compared to filaments comprising one continuous and one discontinuous strand. The strands of filaments comprising at least two continuous strands wind around each other and accumulate torsional stress when twisted. As torsional stress accumulates, the process eventually reaches a limit in which the filament buckles. The introduction of additional twists after the filament has buckled causes the filament to bend forming supercoils or plectonemes. Instead, filaments comprising one continuous and one discontinuous strand have a segment where the only connection between the two sides of the filament is a single strand, for example a single tame molecule, or a single stranded DNA. These filaments do not supercoil because the single strand segment is free to rotate. Consequently, when these filaments are twisted, no torsional stress is accumulated.

Preferably, the target analyte binds to one continuous strand or to the two ends of one discontinuous strand, or the target analyte binds to at least one probe located at one end of one discontinuous strand and to at least one probe located at the other end of the discontinuous strand, within the active segment. Preferably, if the target binds to a strand either continuous or discontinuous, the strands of the active segment and the target analyte are nucleic acids. Preferably, if the target binds to probes located at each end of a discontinuous strand, the target analyte is not a nucleic acid.

In one embodiment, the binding of the target analyte to the filament is performed prior to attachment of the filament to the detection unit. According to this embodiment, the target analyte is exposed to the filament and binding of the analyte to one continuous strand or to the two ends of one discontinuous strand, or the target analyte binds to at least one probe located at one end of one discontinuous strand and to at least one probe located at the other end of the discontinuous strand, within the active segment of the filament occurs. Following exposure of the target analyte to the filament, the filament is then attached to the detection unit under conditions such that target analyte bound to the filament is not disrupted.

As used herein, a "probe" is a specific binding member, which is covalently or non-covalently attached at one end of a discontinuous strand, capable of binding the target analyte. If a target analyte binds to one or more probes located at one end of the discontinuous strand and binds also to one or more probes located at the other end of the discontinuous strand, then the discontinuous strand becomes a continuous strand. Examples of probes useful in the invention are known by one of skill in the art and include, but are not limited to, an antibody, preferably a monoclonal antibody, a nucleic acid aptamer or peptide aptamer, a "sequence specific polymer', as defined in U.S. Patent Publication No. U.S. 2009/0011946, proteins, peptides, amino acids, carbohydrates, hormones, steroids, vitamins, drugs, including those administered for therapeutic purposes as well as those administered for illicit purposes, bacteria, viruses, oligonucleotides having a sequence that is complementary to at least a portion of a nucleic acid target analyte, and metabolites of or antibodies to any of the above substances bound to the active segment of a filament through covalent or non-covalent attachment.

According to the invention, following the binding of the target analyte to the active segment of the filament, an agent is added to the detection unit or the physical rotation of at least one of the surfaces attached to the filament is initiated. As used herein, an "agent" includes, but is not limited to, "intercalating agents" or "twisting agents" and "breaking agents," which are known to one of skill in the art. The term "twisting agent" includes, but is not limited to, an agent capable of causing the physical rotation of one of the surfaces to which the filament is attached, including small molecules and enzymes capable of binding and twisting the filament. The term "intercalating agent" refers to small molecules capable of binding and twisting a nucleic acid filament. Intercalator molecules intercalate between nucleic acid base pairs and unwind the strands at the intercalation point. Unwinding the strands effectively twists the filament causing the filament to form supercoils or plectonemes. Examples of small molecules suitable for use as intercalator molecules include, but are not limited to, actinomycin D, ethidium bromide, propidium, acridine and its derivatives, such as 9-aminoacridine, profiavine, or quinacrine, daunomycin, berberine, doxorubicin, thalidomide, ellipticine, psoralen and its derivatives, and the commercial dyes Gelred, Geigreen, Sybr Gold or Sybr Green. Exemplary enzymes suitable for use as twisting agents include, but are not limited to, type II topoisomerases, such as DNA gyrase. These enzymes preferably cleave DNA molecules and pass another part of the duplex through the break and finally religate the cut DNA, resulting in a change in the linking number of the molecule.

As used herein, the term "breaking agent" refers to an agent capable of recognizing, binding to, and breaking a continuous strand having a target analyte bound to the active segment of the filament. Examples of breaking agents useful in the invention include, but are not limited to, restriction enzymes or restriction endonucleases. In an exemplary embodiment, one of the continuous strands of the active segment is a DNA oligonucleotide complementary to the target analyte and contains the sequence recognized by a specific restriction enzyme. Upon binding of the target analyte, the binding site for the restriction enzyme is created wherein the restriction enzyme cuts the continuous strand converting the strand to a discontinuous strand, as shown in FIGS. 2A-2C, 3A-3C and 6A-6D In one embodiment, a detection device (40) as shown in FIG. 4 is provided. The device contains a plurality of detection units (41) in a detection device (40). According to this embodiment, as shown in the blown-up view, each detection unit (41) consists of a magnetic nanorod (42) attached by multiple filaments (43) to a substantially flat substrate (44). The flat substrate (44) has a pattern of substantially parallel electrodes (e.g., gold strips) (45) with connecting pads at both ends. A pair of magnets (46) creates a magnetic field that pulls the nanorods away from the flat substrate. The magnetic field also orients the nanorods (42) parallel to the flat substrate (44) and perpendicular to the electrodes (45). According to this embodiment, the apparatus is enclosed within a container, for example a capillary tube or microfluidic system, which provides a liquid environment for the device.

In another aspect of the invention, a method is provided for detecting a target analyte in a sample using the detection unit(s) disclosed herein. According to this aspect of the invention, the methods involve exposing a sainple having a target analyte to the detection unit under conditions such that the target analyte binds to the active segment of the filament, wherein binding of the target analyte to the active segment of the filament causes a first change in the property of the filament; exposing the filament to an agent, wherein the exposure of the filament to an agent generates a second detectable change in the property of the filament; transduction of the second detectable change to a medium which generates a detectable signal; and detection of the signal.

One embodiment of this aspect of the invention is shown in FIG. 1. According to this embodiment, the active segment comprises a continuous strand making up a portion of one strand of a filament and a discontinuous strand making up a portion of another strand of the filament. The two ends of the filament are attached by multiple covalent or non-covalent connections to surfaces (these connections are not shown). The two ends of the discontinuous strand in the active segment are able to bind to portions of the target analyte. Preferably, the discontinuous strand is a nucleic acid wherein its two ends in the active segment are complementary to parts of the target analyte which is also a nucleic acid.

Another embodiment of this aspect of the invention corresponds to a filament having an active segment which comprises a continuous strand making up a portion of one strand of a filament and a discontinuous strand making up a portion of another strand of the filament. The two ends of the filament are attached by multiple covalent or non-covalent connections to surfaces. The two ends of the discontinuous strand in the active segment have one or more covalently or non-covalently attached probes able to bind to portions of the target analyte.

Figure 1B:
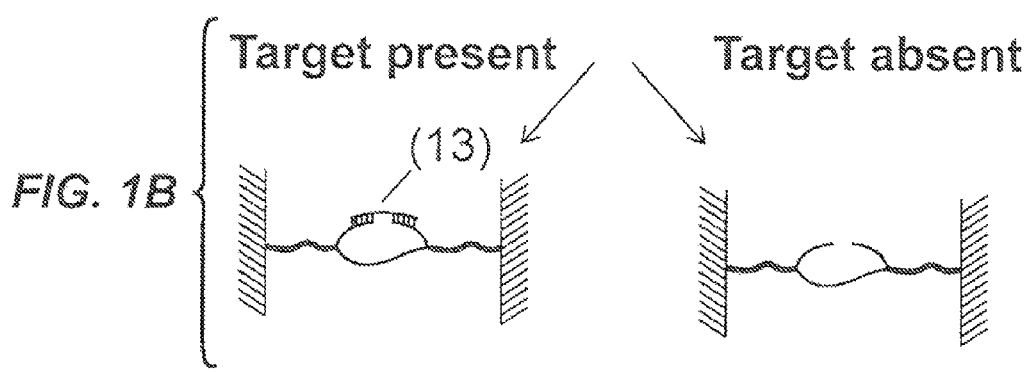
FIG. 1B depicts exposure of the detection unit to a sample under conditions such that if the target analyte (13) is present in the sample then it binds to the discontinuous strand in the active segment resulting in two continuous strands. If the target analyte is not present in the sample, then no changes occur to the active segment.
Figure 1C:
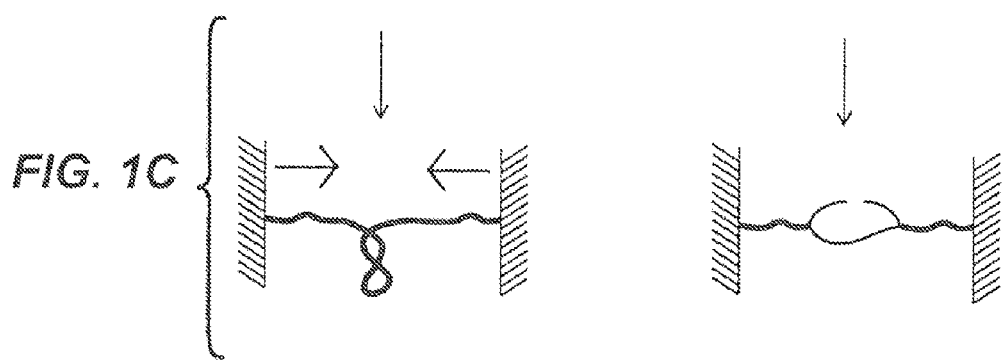
FIG. 1C depicts exposure of the detection unit to a twisting agent or a rotational force. If the active segment comprises two continuous strands as a result of target binding, then the agent or the rotational force twists the filament which results in supercoiling and a force applied by the filament on the surfaces. If the active segment still comprises a continuous and a discontinuous strand, then no significant force is applied on the surfaces. An active segment having one continuous stand and one discontinuous strand which is converted to two continuous strands due to target binding is referred to herein as a "1 to 2 active segment."

According to this and the previous embodiments the detection unit is exposed to the sample under conditions such that the target binds to the active segment if the target is present in the sample. Upon binding of the target analyte to the active segment, the strand is converted from a discontinuous strand to a continuous strand, as shown in FIG. 1B. Initial binding of the target analyte to the filament results in a first property change of the filament. Following binding of the target analyte, the filament having two continuous strands is exposed to a twisting agent or the physical rotation of at least one of the surfaces connected to the filament is initiated. The addition of the twisting agent or physical rotation of one of the surfaces causes the filament to twist and accumulate torsional stress, which is a second property change, as shown in FIG. 1C. As twists are introduced into the extended filament, torsional stress continues to accumulate and eventually the filament buckles. The attractive force between the two surfaces can be detected. An active segment having one continuous stand and one discontinuous strand which is converted to two continuous strands due to target binding is referred to herein as a "1 to 2 active segment".

As used herein, a "property change," "first property change," "second property change," or "change in property of the filament" includes chemical, thermodynamic, mechanical, thermal, electromagnetic and quantum mechanical properties. Exemplary chemical changes include, but are not limited to, changes in chemical bond connectivity, stereochemical configuration, conformation, ionization state, oxidation state or redox potential, and protonation state or pKa. In a preferred embodiment, initial binding of the target analyte to the filament results in a chemical connectivity change, such as the formation of non-covalent bonds (first property change). Exemplary mechanical changes include, but are not limited to, changes in dimension(s), mass density, intramolecular and intermolecular interaction forces, stiffness modulus, strength, fracture toughness, acoustic impedance, and the speed of sound.

According to embodiments, the second detectable change in the filament is transduced to a medium which generates a detectable signal. Examples of the detectable signal which can be generated according to the invention include, but are not limited to, electrical (e.g., capacitance), mechanical, optical, acoustic or thermal signal. In one preferred embodiment, the exposure to a twisting agent results in a change of the filament Intermolecular and intramolecular interaction forces in the specific form of torsional stress (second property change), which ultimately induce filament supercoiling. In another preferred embodiment, the exposure to a breaking agent results in a change of chemical connectivity (second property change).

Figure 10:
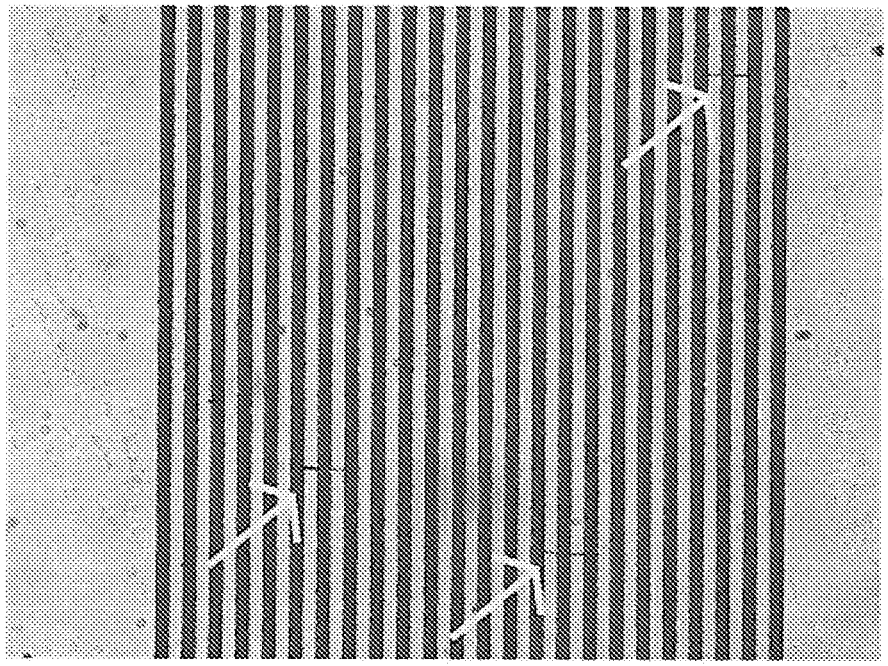
FIG. 10 shows the microscopy image of 20 μm long, 200 nm diameter magnetic nanorods (arrows) on a glass substrate with a gold pattern. Pattern consists of parallel stripes 5 μm wide with 5 μm spacing between them. An external magnetic field created by a pair of magnets orients the nanorods perpendicular to the stripes. The presence of a nanorod in contact with the pattern bridges two stripes allowing electrons to cross. Therefore the presence of a contacting nanorod can be detected from the electrical resistance change between stripes. A resistance change from 1-10 GΩ in the absence of a bridging nanorod to 30-40 kΩ in the presence of a nanorod was measured.
Figure 11A:
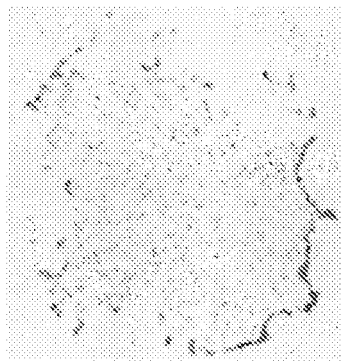
FIG. 11A shows an image of the surface of a charge-coupled device (CCD) sensor obtained using an optical microscope after incubating the surface of the CCD with particles of 1 μm diameter.

In a preferred embodiment of the present invention, the first surface of the detection unit is a particle and the second surface is a substantially flat substrate. A force field acts on the particle and pulls it away from the second surface (e.g. a magnetic field acting on a magnetic particle). Each filament contains at least one active segment comprising one continuous and one discontinuous strand. The device is exposed to a sample in conditions such that if the target is present, then at least one target analyte binds to the active segment of at least one filament. Consequently, a filament having an active segment with two continuous strands is formed (first property change). Upon exposure of the filaments to intercalator molecules, the active segment with the bound target analyte cannot swivel, resulting in the accumulation of torsional stress and supercoiling (second property change). Supercoiling produces a change in distance between the particle and the flat surface which can be detected. Preferably, the movement of the particle towards the surface changes the electrical properties of a non-conductive gap between conductive strips patterned on the surface. For example, if the particle is conductive and elongated, such as a metallic nanorod, upon continued twisting of the filament, the metallic nanorod eventually touches and bridges two conductive strips causing a detectable drop in electrical resistance between the two strips (FIG. 5 and FIG. 10). Alternatively, the change in distance between the surface and the particle can be detected by optical microscopy, either from the reduction of the Brownian motion of the particle (FIG. 9C) or from the change in the diffraction pattern of the particle resulting from the change in distance between the particle and the optical focus (Strick et al., Science 271, 1835 (1996)). Alternatively, the change in distance between the surface and the particle can be detected using an array of light sensors, such as a CCD (FIG. 11).

In one embodiment, a detection device contains a plurality of detection units. The detection device is exposed to the sample in conditions such that the number of target analytes that bind to the detection units is proportional to the concentration of the target analyte. In this manner, the detectable signal is proportional to the concentration of the target analyte, thereby permitting the concentration of the target analyte in the sample to be determined.

Each detection unit may have a plurality of filaments with active segments attached to it, and as a result, each detection unit can bind to a plurality of target analytes.

A detection device may contain several detection units. Furthermore, the device may have a plurality of locations each location with one or more detection units. Each location can be exposed to a different sample. One location can he control-positive location and another, a control-negative location. When testing for a particular condition, for example, an infectious disease, the control-positive location is exposed to a control sample containing one biomarker correlated to the disease. The control-negative location is exposed to a control sample not containing the biomarkers. Other locations are exposed to samples from the patient.

In a further exemplary embodiment, the detectable signal can be the deflection of a deflectable clement, such as a membrane or cantilever. As such, at least one surface of the detection unit is a cantilever. The term "cantilever" or "miero-cantilever" is used herein to denote any structural element that is attached so as to have at least one degree of freedom, enabling movement in at least one dimension. The movement is usually a bending, rotational and/or torsional motion. A cantilever or microcantilever generally has one end fixed to a substrate and an opposite end which is free and unattached. Generally, microcantilevers are preferably made of a semiconductor material. However other materials may be used, provided that such materials are capable of being fabricated in the requisite size, for instance, by a mask aligner. Microcantilevers are of a microscopic size, with a thickness on the order of 1 μm (e.g., 800 nm), a width on the order of 10 μm (e.g. 30 μm), and a length on the order of 100 μm (e.g., 200 or 300 μm). By "micro-membrane" is meant a thin disk or other shape preferably pre-coated with a wide range of films selected from metals, polymers, ceramics to bio-molecules. The micro-membrane may be oscillated at its resonance frequency. A large number of different micromembranes exist, see for example E. Quandt, K. Seemann, Magnetostrictive Thin Film Microflow Devices, Micro System Technologies 96, pp. 451-456, VDE-Verlag GmbH, 1996, which is expressly incorporated herein by reference. According to this embodiment, the detection device can include multiple microcantilevers and/or multiple micro-membranes are part of the present invention.

An additional embodiment of the invention is shown in FIG. 2. As shown in FIG. 2A, the active segment comprises two continuous strands. The first of these strands makes up a portion of a first strand of the filament, and the second of these strands makes up a portion of a second strand of the filament. The two ends of the filament are attached by multiple covalent or non-covalent connections to surfaces (these connections are not shown). The filament is able to supercoil. Preferably, the strands of the active segment and the target analyte are nucleic acids. According to this embodiment, the target analyte is capable of binding to a complementary monomer sequence on one continuous strand, as shown in FIG. 2B, creating a first detectable change. The hybridized region formed contains a binding site for a breaking agent. Addition of the breaking agent results in breaking the continuous strand at the binding site, as shown in FIG. 2C. Exposure of the filament to a twisting agent produces no supercoiling of the filament. In this embodiment, the presence of the target is detected because the filament that initially was able to supercoil, is not able to supercoil after the action of the breaking agent. An active segment having two continuous strands which is converted to one continuous stand and one discontinuous strand due to target binding and exposure to the breaking agent is referred to herein as a "2 to 1 active segment".

Figure 3A:
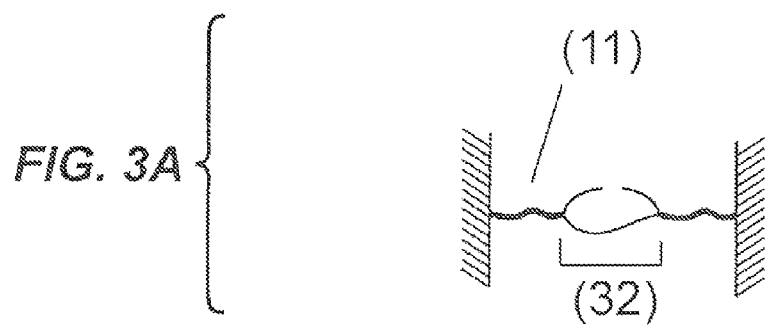
FIG. 3A depicts a detection unit wherein the filament (11) includes an active segment (32) with a continuous single strand and a discontinuous strand.
Figure 3B:
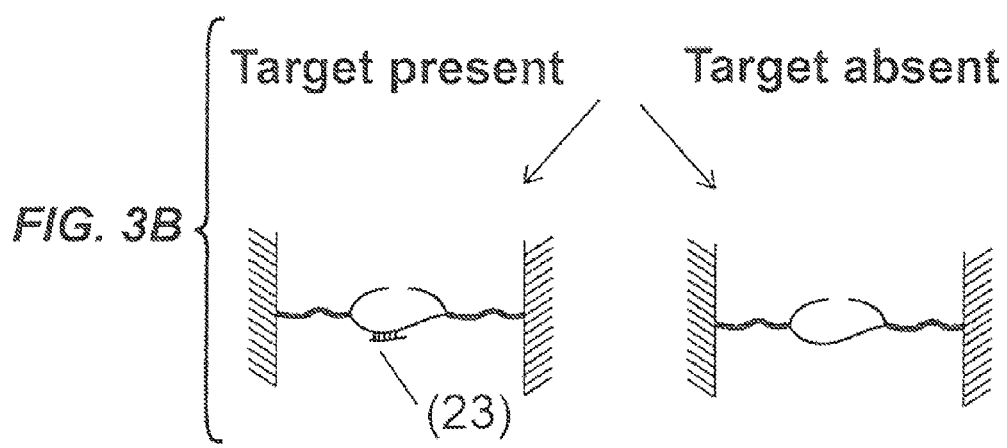
FIG. 3B depicts exposure of the detection unit to a sample under conditions such that if the target analyte (23) is present in the sample then it binds to the continuous strand in the active segment generating a site that can be recognized by a breaking agent. If the target analyte is not present in the sample, then no change occurs to the active segment
Figure 3C:
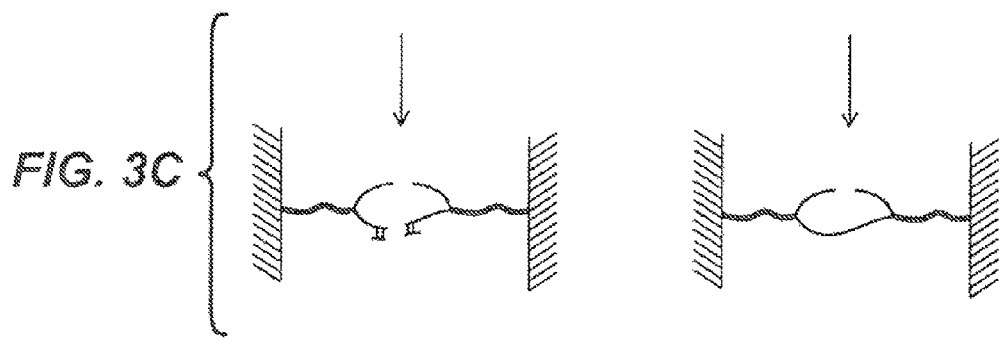
FIG. 3C depicts exposure of the detection unit to a breaking agent. If the target binds the active segment, then the breaking agent breaks the continuous strand of the active segment, dividing the filament in two unconnected segments. An active segment having one continuous stand and one discontinuous strand which is converted to two discontinuous strands due to exposure to the breaking agent is referred to herein as "1 to 0 active segment".
Figure 4:
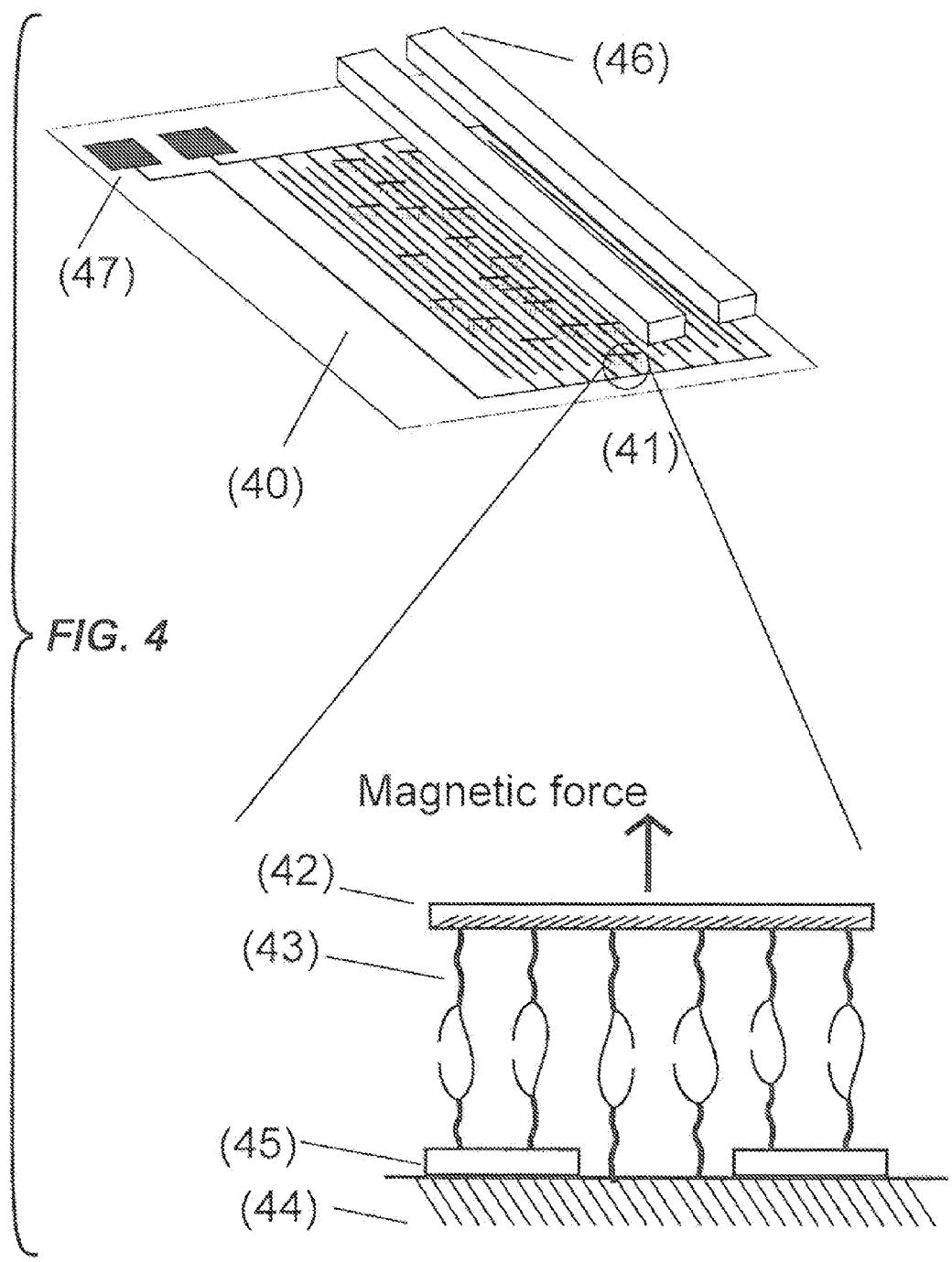
FIG. 4 depicts an embodiment of the detection device (40) of the invention. Multiple detection units (41) having magnetic nanorods (42) are attached by multiple filaments (43) to a flat substrate (44). The flat substrate (44) has parallel strips of electrodes 45) with connecting pads at both ends (47). A pair of permanent magnets (46) creates a magnetic field that pulls the nanorods away from the flat substrate. The magnetic field also orients the nanorods (42) parallel to the flat substrate (44) and perpendicular to the strips of electrodes (45). The device (40) is enclosed within a container (not shown in the figure), for example a capillary tube, which provides a liquid environment for the system.
Figure 6A:
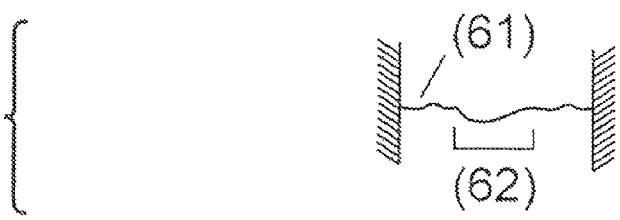
FIG. 6A depicts a detection unit wherein the filament (61) comprises one continuous strand wherein the active segment (62) is part of that strand.
Figure 6B:
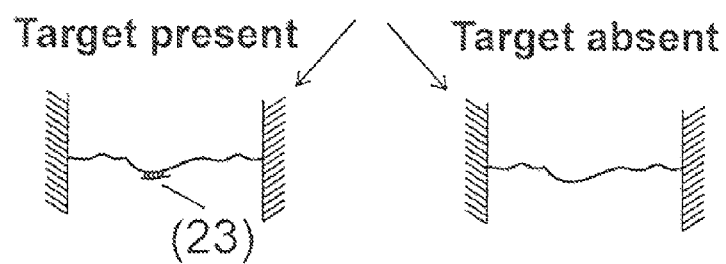
FIG. 6B depicts exposure of the detection unit to a sample under conditions such that if the target analyte (23) is present in the sample then it binds to the strand in the active segment generating a site that can be recognized by a breaking agent. If the target analyte is not present in the sample, then no change occurs to the active segment.
Figure 6C:
FIG. 6C depicts exposure of the detection unit to a breaking agent. If the target binds the active segment, then the breaking agent breaks the strand at the active segment, dividing the filament in two unconnected segments.
Figure 6D:
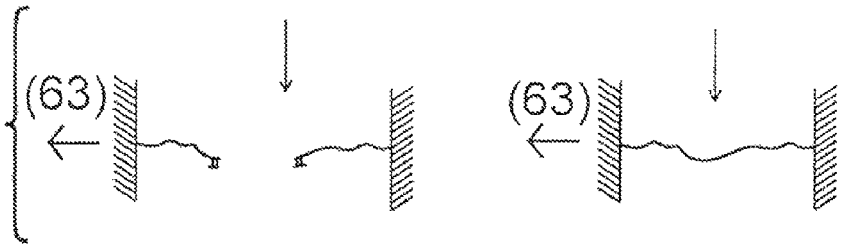
Figure 8A:
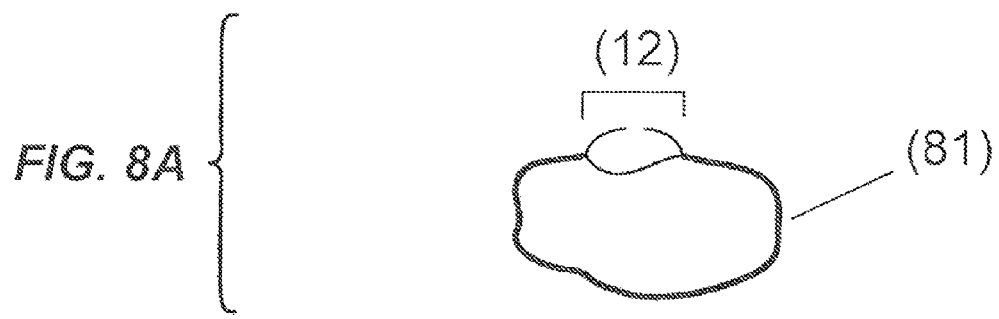
FIG. 8A depicts a circular filament (81) with an active segment (12) comprising a continuous strand and a discontinuous strand.
Figure 8B:
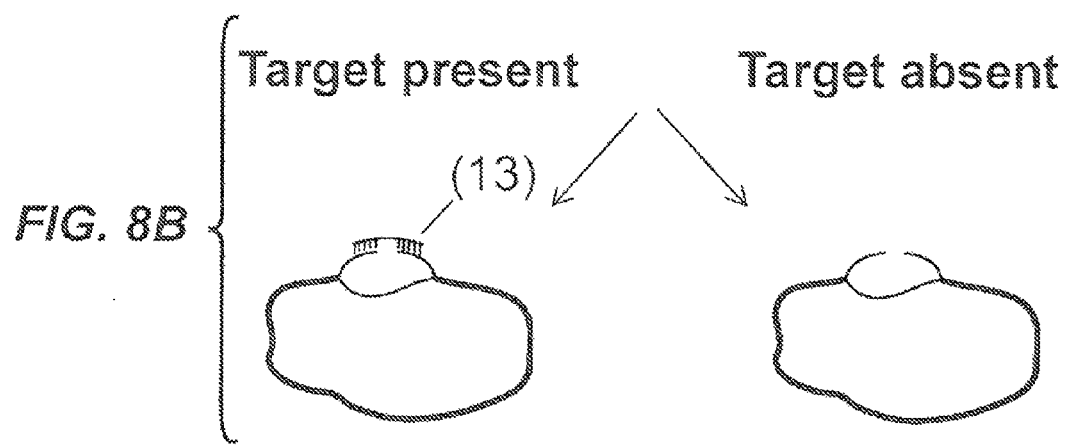
FIG. 8B depicts exposure of the circular filament to a sample under conditions such that if the target analyte (13) is present in the sample then it binds to the discontinuous strand in the active segment resulting in two continuous strands. If the target analyte is not present in the sample, then no changes occur to the active segment.
Figure 8C:
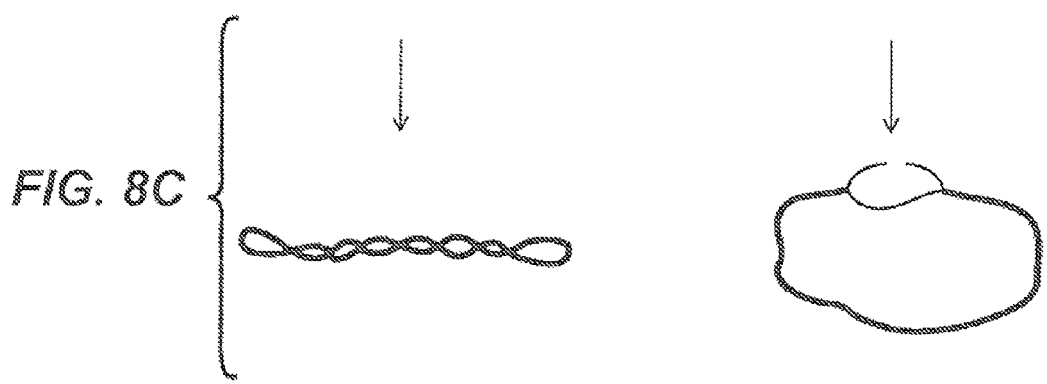
FIG. 8C depicts exposure of the circular filament to a twisting agent. If the active segment comprises two continuous strands as a result of target binding, then the agent twists the filament which results in supercoiling which is a large conformational change that can be detected. If the active segment still comprises a continuous and a discontinuous strand, then no significant conformational change happens.

An additional embodiment of the invention is shown in FIG. 3. As shown in FIG. 3A, the active segment comprises a continuous strand making up a portion of one strand of a filament and a discontinuous strand making up a portion of a second strand of the filament. Preferably, the continuous strand of the active segment and the target analyte are nucleic acids. According to this embodiment, the target analyte is capable of binding to a complementary monomer sequence on the continuous strand, as shown in FIG. 3B, creating a first detectable change. The hybridized region formed contains a binding site for a breaking agent Addition of the breaking agent results in breaking the continuous strand at the binding site, as shown in FIG. 3C, resulting in two discontinuous strands. Upon breaking of the continuous strand, a detectable change in the filament is transduced to a medium which generates a detectable signal. For example, if the detection unit comprise one filament and the first surfaces is a particle under a force that pulls it away from the second surface, then upon breaking of the filament, the distance between the particle and the second surface will increase. This distance change can generate a detectable signal. An active segment having one continuous stand and one discontinuous strand which is converted to two discontinuous strands due to exposure to the breaking agent is referred to herein as a "1 to 0 active segment".

In an additional embodiment, an active segments of the "1 to 0" type described before can have also the functionality of a "1 to 2" type provided the necessary complementary monomer sequences or probes are present. Conversely, a "1 to 2" type can also have the functionality of a "1 to 0" type. Furthermore, once an active segment comprises two strands, for example, after target analyte binding to a "1 to 2" type, then the active segment can behave as a "2 to 1" type of active segment. Moreover, anytime an active segment comprises only one continuous strand, then it can behave as a "1 to 0" type of active segment.

In an additional embodiment, a detection unit can contain several filaments, each with several active segments along its length, capable of binding several target analytes. The detection unit is exposed to the sample and then to breaking agent and twisting agent. The signal obtained depends on the state of each of the active segments of the detection unit. The following are the main possible signals and the conditions that generate them: 1) Distance between surfaces becomes smaller, requires at least one filament to have all its active segments with two or more continuous strands; 2) Distance between surfaces increases, requires every filament to have at least one active segment with no continuous strand (active segments that underwent a "1 to 0" change). This case requires the presence of a force that pulls one surface away from the other. 3) No significant change in distance, in all other cases. For example, a detection unit with two filaments each with two active segments, both of them of the "1 to 2" type. Each of the four active segments have binding sites for a different oligonucleotide, one filament can have sites for A and B, and the other for C and D. The state of the detection unit can be described with a two by two matrix, where each column represents the state of the active segments of one of the filaments. The detection unit is exposed to a sample and then to intercalator molecules, the distance between the surfaces will decrease if A and B are present in the sample or if C and D are present in the sample. This case is shown below in matrix representation:

$$\begin{matrix} 1 & 1 \\ 1 & 1 \end{matrix} \xrightarrow{\text{exposure to sample}} \begin{matrix} 2 & 1 \\ 2 & 1 \end{matrix}$$

In an additional embodiment, a method is provided for identifying two, three, four, five, ten, fifteen, twenty, one hundred, one thousand or more different target analytes in a test sample. According to this embodiment, multiple types of detection units are provided in a detection device. Each type of detection unit contains substantially the same type and number of filaments, and therefore the same active segments. According to this embodiment the detection device may include two, three, four, five, ten, fifteen, twenty, one hundred, one thousand or more different detection units of each type.

Detection units of one type are distinguishable from detection units of another type by at least one physical property (e.g. by their location in the detection device or, when one of the surfaces is a particle, by the electrical properties of the particle). Thus, exposure of the device to a sample (and possible to a breaking agent) changes the state of the detection units in a manner that can be correlated with the target analytes present in the sample and their concentration. Subsequent exposure to a twisting agent produces a change in the distance between the surfaces comprising the devices in accordance with the devices state, in such a way that the detection device can not only sense different target analytes but also identify the specific target analytes present in the sample. According to this embodiment, a method is provided for creating a unique profile or fingerprint of a sample having two, three, four, five, ten, fifteen, twenty, one hundred, one thousand or more different target analytes. As such, profiles from different samples can be stored in a database and/or compared for diagnostic purposes for the detection of diseases or disorders.

EXAMPLE 1

Figure 9A:
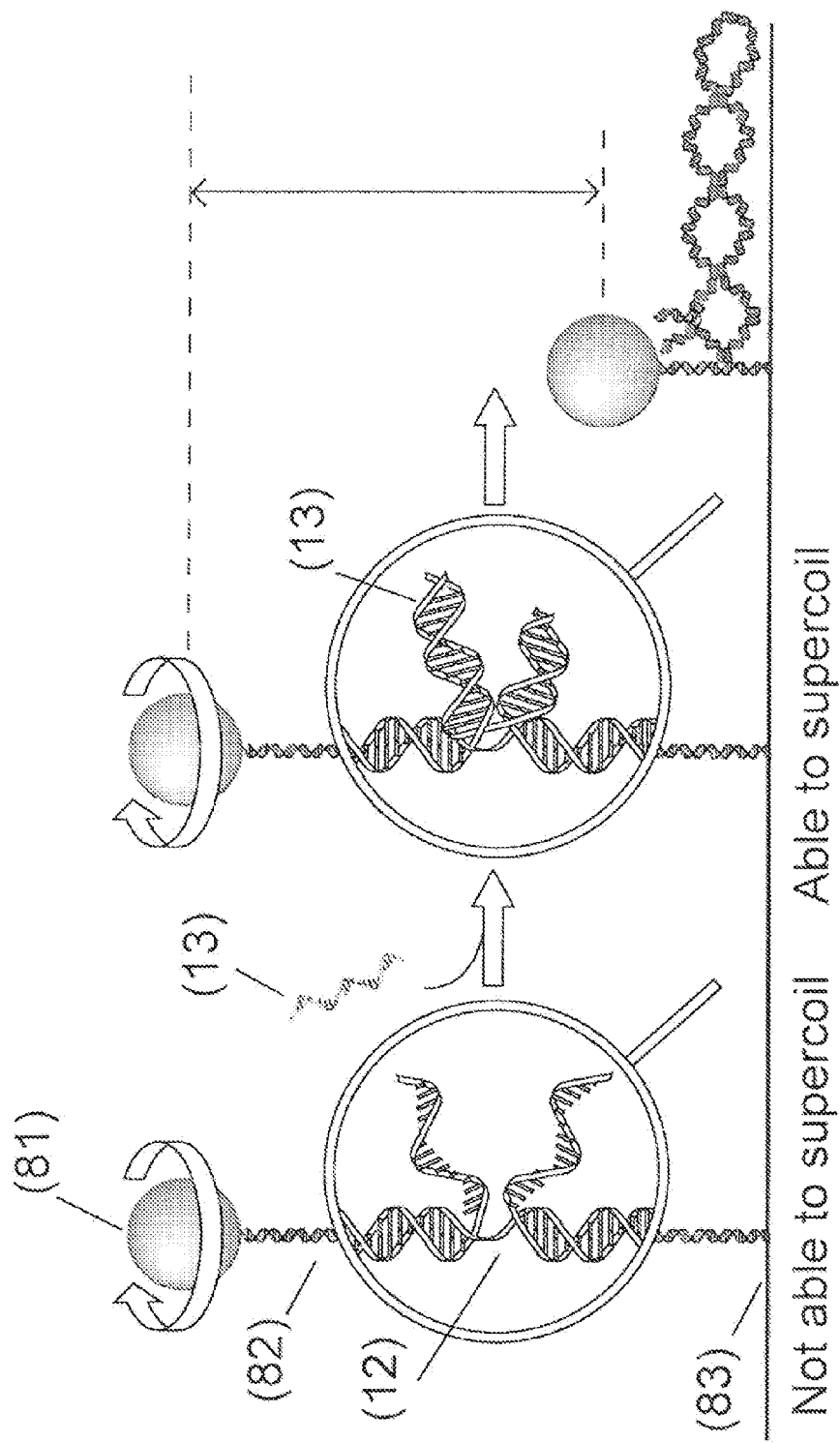
FIG. 9A depicts a detection unit that includes a double stranded DNA molecule (82) attached at one end to a superparamagnetic bead (81) and at the other end to a glass substrate (83). The bead is pulled away from the substrate and rotated by a magnetic field. The active segment (12) includes a continuous strand and a discontinuous strand with unpaired oligonucleotides at both side of the discontinuity. The unpaired oligonucleotides, or overhangs, have sequences complementary to adjacent regions of the target molecule (13). Target hybridization bridges the two sides of the discontinuous strand and therefore it enables supercoiling. Supercoiling produces a large displacement of the magnetic bead which can be detected.
Figure 9B:
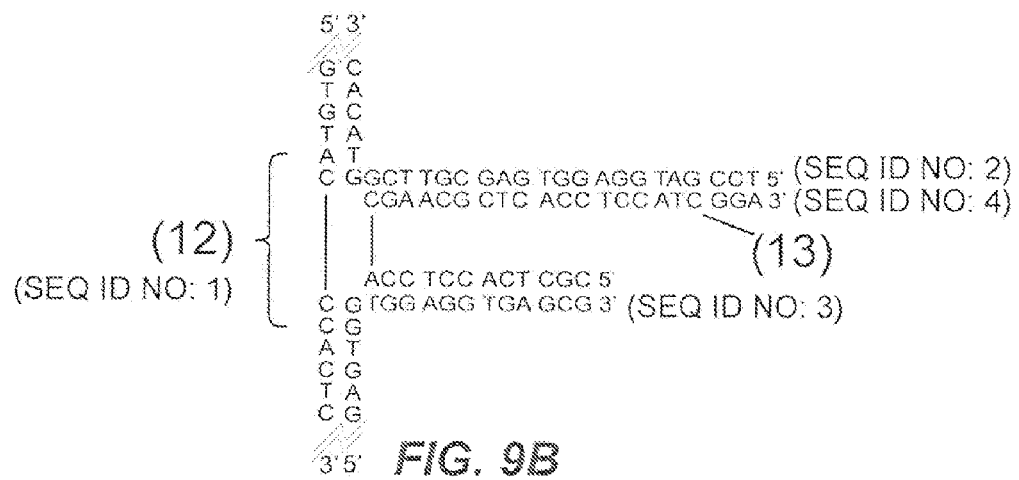
FIG. 9B depicts an exemplary nucleotide sequence of the active segment (12) and the target analyte (13).

Disclosed is a strategy to detect oligonucleotide analytes. In this exemplified detection technique, the hybridization of the target analyte to a DNA molecule restores the capacity of the DNA molecule to supercoil. The detection unit in this example includes a double stranded DNA molecule (dsDNA), 2.5 µm long, attached at one end to a glass surface and at the other end to a 1 µm magnetic bead- a configuration used in magnetic tweezers experiments (see Strick et al., Science 271, 1835-1837 (1996); Geledon et al., Nano Lett 9, 1720 (2009)). (FIG. 9A). A magnetic field pulls the bead away from the glass surface extending the DNA molecule. The DNA molecule has a discontinuous strand and therefore is not able to supercoil (Voet et al., Biochemistry. 4th edn, John Wiley & Sons, Inc., Hoboken, N.J., USA, 2011). The two unpaired overhangs at both sides of the discontinuous strand are each complementary to adjacent regions of the target molecule, Hybridization of a target molecule to both overhangs bridges the two sides of the strand and restores the capacity of the dsDNA molecule to supercoil (FIG. 9B). Supercoiling is induced by rotation of the magnetic field, which rotates the bead and twists the molecule. The conformational transition from extended to supercoiled DNA displaces the bead a distance equivalent to the molecule length (FIG. 9A).

Figure 9C:
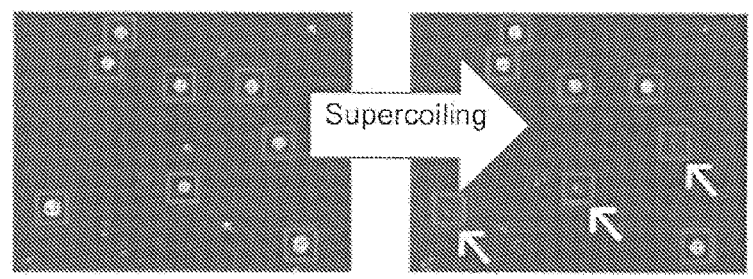
FIG. 9C shows images used to detect the extended/supercoiled transition by video microscopy. The magnetic beads of detection units are visible under an optical microscope. Subtraction of consecutive video microscopy frames generates white spots at the positions where beads are moving and therefore tethered by an extended DNA molecule. Supercoiled detection units are clearly differentiated from the reduction in bead movement (arrows).

In this example, the conformational state of multiple detection units is monitored simultaneously by video-microscopy (FIG. 9C). Examples 2 and 3 exemplify alternative strategies. In the video-microscopy strategy, the state of DNA molecules is detected from movement of the head. Beads tethered by an extended DNA molecule undergo ample Brownian fluctuations and therefore appear as white, rounded regions in an image obtained by subtraction of successive video frames (FIG. 9C, left image). Beads non-specifically bound to the glass are readily screened out of the analysis as they move significantly less than DNA tethered beads. The beads are rotated 60 turns, which twists the DNA molecules sufficiently to induce supercoiling in the detection units bound to a target oligonucleotide. Then, new video frames are acquired and analyzed. Beads tethered by supercoiled DNA molecules have a restricted motion and appear smaller and black or dark gray (FIG. 9C, right image). The output of the code is the "supercoiled fraction," the number of detection units that stop moving (supercoiled) divided by the total number of detection units present in the image.

Figure 9D:
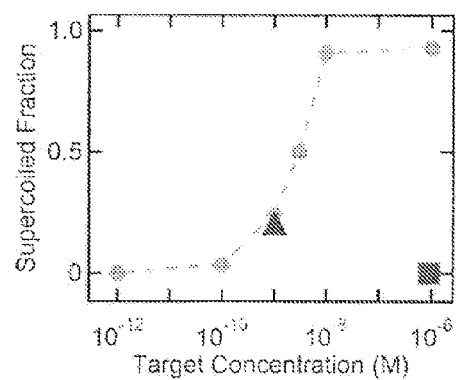
FIG. 9D shows the fraction of detection units that supercoil after 15 minutes of incubation with target molecules at room temperature. Each data point represents a separate experiment. Circles and triangle symbols represent measurements using target molecules containing a sequence complementary to the active segment overhangs. The circles represent measurements obtained in purified samples; instead, the triangle symbol shows a measurement obtained in an EDTA treated saliva sample. The square symbol is a control measurement of a target with nucleotide sequence non-complementary to the active segment overhangs.

The detection strategy was tested using detection units that had the active segment and the target shown in FIG. 9B. Detection units were incubated with the target for 15 minutes before rotating the beads. FIG. 9D shows the observed supercoiled fraction as a function of target concentration. Fractions shown by each data point are the actual number of supercoiled detection units over the total number of detection units measured. The detection system saturated at target concentrations of approximately 10 nM at which almost all the detection units supercoiled. The minimum supercoiled fraction that the system can detect is inversely proportional to the number of monitored detection units. Therefore, by increasing the number of monitored detection units, the concentration that the system can detect decreases. We observed supercoiling after incubation for 15 minutes with target molecules at 1 pM concentration by monitoring ~4,000 detection units.

Detailed Experimental Method

DNA preparation. Functionalized dsDNAs were generated following a previously described procedure (Celedon et al., Nano Lett 9, 1720 (2009). In order to incorporate the active segment, an additional ligation step was conducted. Briefly, two DNA segments, 1 kilo base pair (kbp) long, were generated by PCR in the presence of modified nucleotides, either biotin-14-dCTP (Life Technologies, Carlsbad, U.S.) or digoxigenin-11-dUTP (Roche, Indianapolis, U.S.). The biotinylated segment was ligated to a 1 kbp DNA segment. The active segment (FIG. 9B) was constituted by hybridization of synthetic DNA oligos (integrated DNA Technologies, Coralville, U.S.). A 7 kbp plasmid was linearized with the restriction enzyme XbaI (New England BioLabs, Ipswich, U.S) and then ligated in the presence of XbaI and NheI (New England BioLabs) to the active segment and to the digoxigenin segment, both of which had NMI overhangs. The product was purified and then ligated to the biotinylated segment using a similar ligation reaction in the presence of the restriction enzymes BamHI and BglII.

Device assembly. Borosilicate capillary tubes (Vitrocom, Mountain Lakes, US) were washed with ethanol and deionized water and dried with nitrogen gas. The interior of the tubes was functionalized by incubation in Standard Buffer with 100 mM NaCl (SB100) (10 mM phosphate buffer, pH 7.2, 0.1% Tween-20) complemented with 0.1 mg/ml anti-digoxigenin (Polyclonal, Roche) for 1 hour at room temperature. Then, the capillaries were blocked by incubation with SB100 complemented with 50 mg/ml Bovine Serum Albumin (Sigma Aldrich, St. Louis, U.S.) for 1 hour at room temperature. Functionalized capillary tubes were incubated with approximately 1 ng of functionalized DNA molecules for 10 minutes. Streptavidin functionalized superparamagnetic beads (1 µm, Myone, Life Technologies) were flowed into the capillary tube and incubated for 10 minutes. Unbound beads were removed by flowing SB500 (SB with 500 mM NaCl). Two cube permanent magnets (5 mm side, N42) (K&J Magnetics, Inc., Jamison, U.S.) separated by 2 mm from each other were placed 5 mm above the capillaries to lift the beads away from the glass surface. The orientation of the magnets was such that their magnetization was in opposite directions and perpendicular to the capillary tubes.

Detection of single molecule hybridization by video-microscopy. SB500 containing the target oligonucleotide was flowed into the capillary using a syringe pump and incubated at room temperature for 15 minutes (*). Video microscopy of the beads was obtained using an inverted optical microscope (Nikon, TS100) with bright field illumination and equipped with a digital camera connected to a PC. The camera was either a MicroPublisher 5.0 (Qimaging, Surrey, Canada) or QICAM (Qimaging). A low amplification objective (40×) was used in order to visualize a large number of beads (detection units) in a single field of view. An image analysis code written in Matlab was used to detect the state (extended/supercoiled) of all the detection units in the field of view simultaneously. Beads tethered by an extended non-supercoiled DNA molecule undertake large Brownian fluctuations (≈1 µm). The Matlab code detected this movement by acquiring 100 monochromatic frames and summing the square difference of successive frames, according to the formula, $M=\Sigma_{i=1}^{99}(I_{i+1}-I_i)^2$ where $I_i$ is the ith frame. FIG. 9C (left) shows an example of the resulting image, $M_1$. Beads tethered by an extended DNA molecule produced white rounded regions instead, beads that were non-specifically attached to the glass substrate appeared as small gray spots. After the code had automatically identified the extended DNA molecules (blue squares in FIG. 1c), the external magnets were rotated 60 turns to rotate beads and twist the DNA molecules. Then, a second set of 100 images was acquired and the above formula was applied again to obtain a second image, $M_2$ (FIG. 1c, right). The code detected whether or not a particular detection unit supercoiled by comparing the average pixel intensity in the region before and after bead rotation. The output of the code was the supercoiled fraction, i.e. the number of beads that stop moving (supercoiled) divided by the number of beads that were initially moving. (*) Note: For the control experiment using saliva, the sample was prepared by mixing one part of saliva with one part of enzyme inhibitor buffer (313 mM EDTA, 0.5% SDS, 500 mM NaCl). This solution was incubated for 1 hour at 55° C., filtered with a 0.2 µm filter, spiked with oligonucleotide targets and flowed in the capillary tube.

EXAMPLE 2

This example discloses a method to detect the presence of nanorods contacting a flat surface. The method can be used to detect supercoiling of a DNA molecule if the molecule is previously attached at one end to a nanorod and at the other end to the flat surface.

The presence of nanorods contacting a gold pattern was detected from the drop in electrical resistance between gold stripes (FIG. 10). A resistance change from 1-10 GΩ in the absence of a bridging nanorod to 30-40 kΩ in the presence of a nanorod was measured. Simple hand held testers can detect this resistance change.

Nanorods were prepared by electrodeposition into the 200 nm diameter pores of an aluminum oxide template membrane (Whatman, Springfield Mill, Kent, England), similar to previously published protocols. (Celedon et al., Nano Lett 9, 1720 (2009)). The nanorods formed by filling the pores of the membrane by the deposited material. Segments were deposited by changing the electrolytic solution. The template was finally etched to generate the nanorods. Pt/Ni nanorods about 20 µm long with 1 µm nickel segment were produced.

The patterned surface and the nanorods were separately incubated for 10 min in 10 mM phosphate buffer complemented with 1 mg/ml BSA (Sigma-Aldrich, St Louis, Mo., USA). The resistance between consecutive stripes and then applied a 1 µl drop containing nanorods to the surface was measured. We let dry for 30 min in the presence of a magnetic field that oriented the nanorods perpendicular to the gold stripes. Microscopy images of the nanorods on the gold pattern were taken (FIG. 10). The resistance between consecutive stripes was then again measured. Consecutive stripes without nanorods between them had resistances between 1-10 GΩ. Stripes with nanorods bridging them had resistances between 30-40 kΩ. Therefore the presence of one nanorod produces a 6 order of magnitude change in the electrical resistance between stripes that can be readily detected.

EXAMPLE 3

This example discloses a method to detect the presence of a particle in the vicinity of an array of light sensors, such as complementary metal-oxide-semiconductor (CMOS) and charge-coupled devices (CCD), normally used in digital video cameras. The method can be used to detect supercoiling of a DNA molecule if the molecule is previously attached at one end to a particle and at the other end to the surface of the sensor.

Figure 11B:
FIG. 11B shows an image acquired using the CCD sensor of FIG. 11A which reveals the presence of the particles without using a microscope (see text m Example 3).

The presence of 1 µm beads (Myone, Life Technologies) was detected on the surface of a CCD camera. Beads were placed directly on the surface of the sensor. A 2 µl drop of solution containing the beads was placed on the surface. After few minutes, the water in the solution had evaporated and an image of the surface of the sensor was obtained using an optical microscope (FIG. 11A), showing a large number of beads on the surface. The sensor was then introduced in a sealed box having only one small hole through which light from a light-emitting diode (LED) entered the box. The light illuminated the surface of the sensor. Acquiring an image using the camera under these conditions revealed the presence of the particles (FIG. 11B). Particles on the surface of the sensor block part of the light producing a decrease of intensity at some pixels.

A modification of this method is to use fluorescent particles and instead of detecting a decrease in the light intensity, detect an increase in light intensity as a result of the presence of the particles.

All references cited in this disclosure are incorporated by reference to the same extent as if each reference had been incorporated by reference in its entirety individually.

While the invention has been described in detail and with reference to specific embodiments thereof, it will be readily apparent to one of ordinary skill in the relevant arts that other suitable modifications and adaptations to the methods and applications described herein can be made without departing from the scope of any of the embodiments.

results in a continuous strand becoming discontinuous and the active segment becoming incapable of accumulating torsional stress;

(b) exposing the at least one filament to one or more of a twisting agent or a rotational force, wherein the exposure of the at least one filament to the one or more of the twisting agent or rotational force generates a detectable change in a property of the at least one filament; and

What is claimed is:

1. A method of detecting a target analyte in a sample, the method comprising:
   (a) exposing a sample containing a target analyte to at least one filament comprising at least two nucleic acid strands, wherein at least one nucleic acid strand comprises an active segment, under conditions such that the target analyte binds to the active segment of the at least one filament and optionally exposing the active segment to a breaking agent, wherein binding of the target analyte to the active segment either results in a discontinuous strand becoming continuous and the active segment becoming capable of accumulating torsional stress, or (c) detecting the detectable change; wherein the at least one filament has been attached by at least two connections to each of a first and second surface, before conducting step (b); wherein the first and second surfaces are separated by a linear force and when the target analyte binds the at least one filament, the tension of the at least one filament upon addition of the twisting agent or application of a rotational force exceeds the linear force such that the first and second surfaces contact each other to form an electrical circuit.

2. A method of detecting a target analyte in a sample, the method comprising:

(a) exposing a sample containing a target analyte to at least one filament comprising at least two nucleic acid strands, wherein at least one nucleic acid strand comprises an active segment, under conditions such that the target analyte binds to the active segment of the at least one filament and optionally exposing the active segment to a breaking agent, wherein binding of the target analyte to the active segment either results in a discontinuous strand becoming continuous and the active segment becoming capable of accumulating torsional stress, or results in a continuous strand becoming discontinuous and the active segment becoming incapable of accumulating torsional stress;

(b) exposing the at least one filament to one or more of a twisting agent or a rotational force, wherein the exposure of the at least one filament to the one or more of the twisting agent or rotational force generates a detectable change in a property of the at least one filament; and (c) detecting the detectable change; wherein the at least one filament has been attached by at least two connections to each of a first and second surface, before conducting step (b); wherein the first surface is a nanorod and the second surface is a flat surface having a series of conductive electrodes separated by non-conductive material, wherein a magnetic force imposed on the nanorod orients the nanorod substantially parallel to the second surface and substantially perpendicular to the conductive electrodes.

3. A method of detecting a target analyte in a sample, the method comprising:

(a) exposing a sample containing a target analyte to at least one filament comprising at least two nucleic acid strands, wherein at least one nucleic acid strand comprises an active segment, under conditions such that the target analyte binds to the active segment of the at least one filament and optionally exposing the active segment to a breaking agent, wherein binding of the target analyte to the active segment either results in a discontinuous strand becoming continuous and the active segment becoming capable of accumulating torsional stress, or results in a continuous strand becoming discontinuous and the active segment becoming incapable of accumulating torsional stress;

(b) exposing the at least one filament to one or more of a twisting agent or a rotational force, wherein the exposure of the at least one filament to the one or more of the twisting agent or rotational force generates a detectable change in a property of the at least one filament; and (c) detecting the detectable change; wherein the at least one filament has been attached by at least two connections to each of a first and second surface, before conducting step (b); wherein the first surface is a conductive or semiconductive particle and the second surface has electrodes separated by non-conductive gap; the first and second surfaces are separated by a linear force and when the target analyte binds the at least one filament, the tension of the at least one filament upon addition of the twisting agent or application of a rotational force exceeds the linear force such that the distance between the two surfaces decreases producing a detectable change of an electrical property of the non-conductive gap between the electrodes.

4. A method of detecting a target analyte in a sample, the method comprising:

(a) exposing a sample containing a target analyte to at least one filament comprising at least two nucleic acid strands, wherein at least one nucleic acid strand comprises an active segment, under conditions such that the target analyte binds to the active segment of the at least one filament and optionally exposing the active segment to a breaking agent, wherein binding of the target analyte to the active segment either results in a discontinuous strand becoming continuous and the active segment becoming capable of accumulating torsional stress, or results in a continuous strand becoming discontinuous and the active segment becoming incapable of accumulating torsional stress;

(b) exposing the at least one filament to one or more of a twisting agent or a rotational force, wherein the exposure of the at least one filament to the one or more of the twisting agent or rotational force generates a detectable change in a property of the at least one filament; and (c) detecting the detectable change; wherein the at least one filament has been attached by at least two connections to each of a first and second surface, before conducting step (b); wherein the at least one filament comprises at least one continuous nucleic acid strand and at least one discontinuous nucleic acid strand, wherein the two ends of the at least one discontinuous nucleic acid strand are capable of binding to different portions of the target analyte, wherein binding of the target analyte to the active segment results in a discontinuous strand becoming continuous and the active segment becoming capable of accumulating torsional stress.

5. A method of detecting a target analyte in a sample, the method comprising:

(a) exposing a sample containing a target analyte to at least one filament comprising at least two nucleic acid strands, wherein at least one nucleic acid strand comprises an active segment, under conditions such that the target analyte binds to the active segment of the at least one filament and optionally exposing the active segment to a breaking agent, wherein binding of the target analyte to the active segment either results in a discontinuous strand becoming continuous and the active segment becoming capable of accumulating torsional stress, or results in a continuous strand becoming discontinuous and the active segment becoming incapable of accumulating torsional stress;

(b) exposing the at least one filament to one or more of a twisting agent or a rotational force, wherein the exposure of the at least one filament to the one or more of the twisting agent or rotational force generates a detectable change in a property of the at least one filament; and (c) detecting the detectable change; wherein the at least one filament has been attached by at least two connections to each of a first and second surface, before conducting step (b); wherein the at least one filament comprises at least two continuous single stranded nucleic acids capable of accumulating torsional stress, wherein binding of the target analyte to the active segment of one of the at least two continuous single stranded nucleic acids results in a continuous double stranded nucleic acid, and wherein exposing said continuous double stranded nucleic acid to a breaking agent cleaves the continuous double stranded nucleic acid, resulting in the continuous double stranded nucleic acid becoming a discontinuous nucleic acid strand and the active segment becoming incapable of accumulating torsional stress.

* * * * *

SEQUENCE LISTING

```
<160> NUMBER OF SEQ ID NOS: 4

<210> SEQ ID NO 1
<211> LENGTH: 12
<212> TYPE: DNA
<213> ORGANISM: Artificial Sequence
<220> FEATURE:
<223> OTHER INFORMATION: Sequence randomly generated.

<400> SEQUENCE: 1
gtgtacccac tc                                                          12

<210> SEQ ID NO 2
<211> LENGTH: 27
<212> TYPE: DNA
<213> ORGANISM: Artificial Sequence
<220> FEATURE:
<223> OTHER INFORMATION: Sequence randomly generated.

<400> SEQUENCE: 2
tccgatggag gtgagcgttc ggtacac                                          27

<210> SEQ ID NO 3
<211> LENGTH: 18
<212> TYPE: DNA
<213> ORGANISM: Artificial Sequence
<220> FEATURE:
<223> OTHER INFORMATION: Sequence randomly generated.

<400> SEQUENCE: 3
gagtggtgga ggtgagcg                                                    18

<210> SEQ ID NO 4
<211> LENGTH: 33
<212> TYPE: DNA
<213> ORGANISM: Artificial Sequence
<220> FEATURE:
<223> OTHER INFORMATION: Sequence randomly generated.

<400> SEQUENCE: 4
cgctcacctc cacgaacgct cacctccatc gga                                   33
```